(12) United States Patent
Tsuruta

(10) Patent No.: US 12,714,294 B2
(45) Date of Patent: Aug. 25, 2026

(54) INSERTION DEVICE, BENDING PORTION OF INSERTION DEVICE, AND TRACTION MEMBER FOR BENDING PORTION OF INSERTION DEVICE

(71) Applicant: OLYMPUS MEDICAL SYSTEMS CORP., Tokyo (JP)

(72) Inventor: Hiroshi Tsuruta, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 594 days.

(21) Appl. No.: 17/953,879

(22) Filed: Sep. 27, 2022

(65) Prior Publication Data

US 2023/0099459 A1 Mar. 30, 2023

Related U.S. Application Data

(60) Provisional application No. 63/249,632, filed on Sep. 29, 2021.

(51) Int. Cl.
*A61B 1/005* (2006.01)
*A61B 1/00* (2006.01)
(Continued)

(52) U.S. Cl.
CPC ........ *A61B 1/0055* (2013.01); *A61B 1/00105* (2013.01); *A61B 1/008* (2013.01); *G02B 23/2484* (2013.01); *G02B 23/26* (2013.01)

(58) Field of Classification Search
CPC ... A61B 1/0055; A61B 1/00105; A61B 1/008; A61B 1/0057; A61B 2017/003;
(Continued)

(56) References Cited

U.S. PATENT DOCUMENTS 4,686,963 A * 8/1987 Cohen .................. A61B 1/0055 138/120
2009/0105542 A1 4/2009 Kitagawa et al.
(Continued)

FOREIGN PATENT DOCUMENTS

JP S63-315026 A 12/1988
JP H05-305052 A 11/1993
(Continued)

*Primary Examiner* — Anh T Nguyen
*Assistant Examiner* — Rynae E Boler
(74) *Attorney, Agent, or Firm* — Morgan, Lewis & Bockius LLP

(57) ABSTRACT

An insertion device comprising an insertion portion configured to be inserted into a subject and having a longitudinal axis in a state of forming a straight line. A bending portion is provided at a distal end side of the insertion portion. A bending tube is provided in the bending portion. A traction member is disposed in the bending portion. The bending tube includes a first joint ring and a second joint ring. The first joint ring is joined to the second joint ring in an adjacent manner. The first joint ring has a first contact portion where the traction member contacts an outer peripheral portion of the first joint ring. The second joint ring has a second contact portion where the traction member contacts an inner peripheral portion of the second joint ring. Application of tension on the traction member bends the bending portion.

22 Claims, 20 Drawing Sheets

(51) Int. Cl.
*A61B 1/008* (2006.01)
*G02B 23/24* (2006.01)
*G02B 23/26* (2006.01)

(58) Field of Classification Search
CPC ........... A61B 2017/00314; A61B 2017/00318; A61B 2017/00323; A61B 2017/00327; A61B 1/005; A61B 1/0051; A61B 1/0052; A61B 1/0053; A61B 1/0056; A61B 1/0058
See application file for complete search history.

(56) References Cited

U.S. PATENT DOCUMENTS

| | | | | |
|---|---|---|---|---|
| 2009/0137875 | A1 * | 5/2009 | Kitagawa ............. | A61B 1/0055 600/146 |
| 2012/0071720 | A1 * | 3/2012 | Banik .................... | A61B 1/018 600/118 |
| 2021/0219821 | A1 * | 7/2021 | Appling ............... | A61B 1/0056 |

FOREIGN PATENT DOCUMENTS

| | | | | |
|---|---|---|---|---|
| JP | H06-285010 | A | | 10/1994 |
| JP | 2000-296103 | A | | 10/2000 |
| JP | 2005-007068 | A | | 1/2005 |
| JP | 2007-215932 | A | | 8/2007 |
| JP | 2009-261587 | A | | 11/2009 |
| JP | 4740702 | B2 | | 8/2011 |
| JP | 2017217293 | A | * | 12/2017 |
| WO | 2021/199180 | A1 | | 10/2021 |

* cited by examiner

20
T
24
25
22a
22
OF
22b
21c
21a
21
27
IF
23
21b
22c
V
IV
A
X
UP
DOWN

T
R
24
25
22
OF
IF
21
OF
IF
22
OF
OF
IF
IF
21
20a
21
22
21
22
20
UP
DOWN 20
22
28
21
27
28
22
28
21
27
28
22
24
25
23
28
22b
21c
21b
23
27
22c
22b
21c
21b
22c
28
23
28
23
27
28
UP
DOWN 20
24
22a
22
29
22b
21c
21a
27
21
21b
22c
25
23
UP
DOWN
X

UP DOWN 20
24
22a
22
28
22b
21c
21a
27
21
21b
22c
23
25
UP
DOWN
X

INSERTION DEVICE, BENDING PORTION OF INSERTION DEVICE, AND TRACTION MEMBER FOR BENDING PORTION OF INSERTION DEVICE

RELATED APPLICATION DATA

This application is based on and claims priority under 35 U.S.C. § 119 to U.S. Provisional Application No. 63/249,632 filed on Sep. 29, 2021, the entire contents of which are incorporated herein by reference.

FIELD OF THE DISCLOSURE

The disclosure relates to an insertion device in which an insertion portion includes a bending portion which is bent when a wire is pulled, to the bending portion of the insertion device, and to a traction member for the bending portion.

BACKGROUND

In recent years, endoscopes, which are one type of insertion device, have been widely used in a medical field and an industrial field. Endoscopes allow observation and treatment of a site to be examined inside a subject by inserting an elongated insertion portion into the subject. For such an endoscope, there is a known configuration in which a bendable bending portion is provided in the insertion portion.

The bending portion of the endoscope is provided to improve ease of advance of the insertion portion at a bent part of a conduit and, in addition to the above, to vary an observation direction of an observation optical system provided at a distal end portion located at a position forward of the bending portion.

For example, Japanese Patent Application Laid-Open Publication No. 2005-7068 discloses a configuration of a bending portion where a plurality of bending pieces is continuously provided in a direction of a longitudinal axis and a plurality of wires penetrate through wall portions of these bending pieces.

SUMMARY OF THE DISCLOSURE

An aspect of the present disclosure is directed to an insertion device comprising an insertion portion configured to be inserted into a subject and having a longitudinal axis in a state of forming a straight line. A bending portion is provided at a distal end side of the insertion portion. A bending tube is provided in the bending portion. A traction member is disposed in the bending portion. The bending tube includes a first joint ring and a second joint ring. The first joint ring is joined to the second joint ring in an adjacent manner. The first joint ring has a first contact portion where the traction member contacts an outer peripheral portion of the first joint ring. The second joint ring has a second contact portion where the traction member contacts an inner peripheral portion of the second joint ring. Application of tension on the traction member bends the bending portion.

Another aspect of the present disclosure is directed to a bending portion of an insertion device. The bending portion includes a bending tube and a traction member. The bending tube includes a first joint ring and a second joint ring. The first joint ring is joined to the second joint ring in an adjacent manner. The traction member contacts an outer peripheral portion of the first joint ring at a first contact portion. The traction member contacts an inner peripheral portion of the second joint ring at a second contact portion. Application of tension on the traction member bends the bending portion.

BRIEF DESCRIPTION OF THE DRAWINGS

FIG. 17 is a partial cross-sectional view showing a state where the bending tube of the first modification having the tapered surfaces serving as the wire escape portions is bent upward;

DETAILED DESCRIPTION OF THE PREFERRED EMBODIMENTS

Hereinafter, description will be made by taking an endoscope as an example of an insertion device. In the description made hereinafter, drawings based on respective embodiments are schematic views. Note that relationships between a thickness and a width of respective parts, thickness ratios between the respective parts, and the like differ from actual ones. Some parts may have different dimensional relationships or different size ratios between drawings.

In the description made hereinafter, an endoscope for urinary organs where an insertion portion has a small-diameter, such as a ureteropelvic endoscope, is shown as an example of the insertion device.

The endoscope is not limited to a ureteropelvic endoscope, and is also applicable to various so-called flexible endoscopes and so-called rigid endoscopes, the flexible endoscopes having a flexible insertion portion to be inserted into the upper or lower digestive organs of a living body, the rigid endoscopes having a rigid insertion portion used for surgical purposes.

Figure 1:
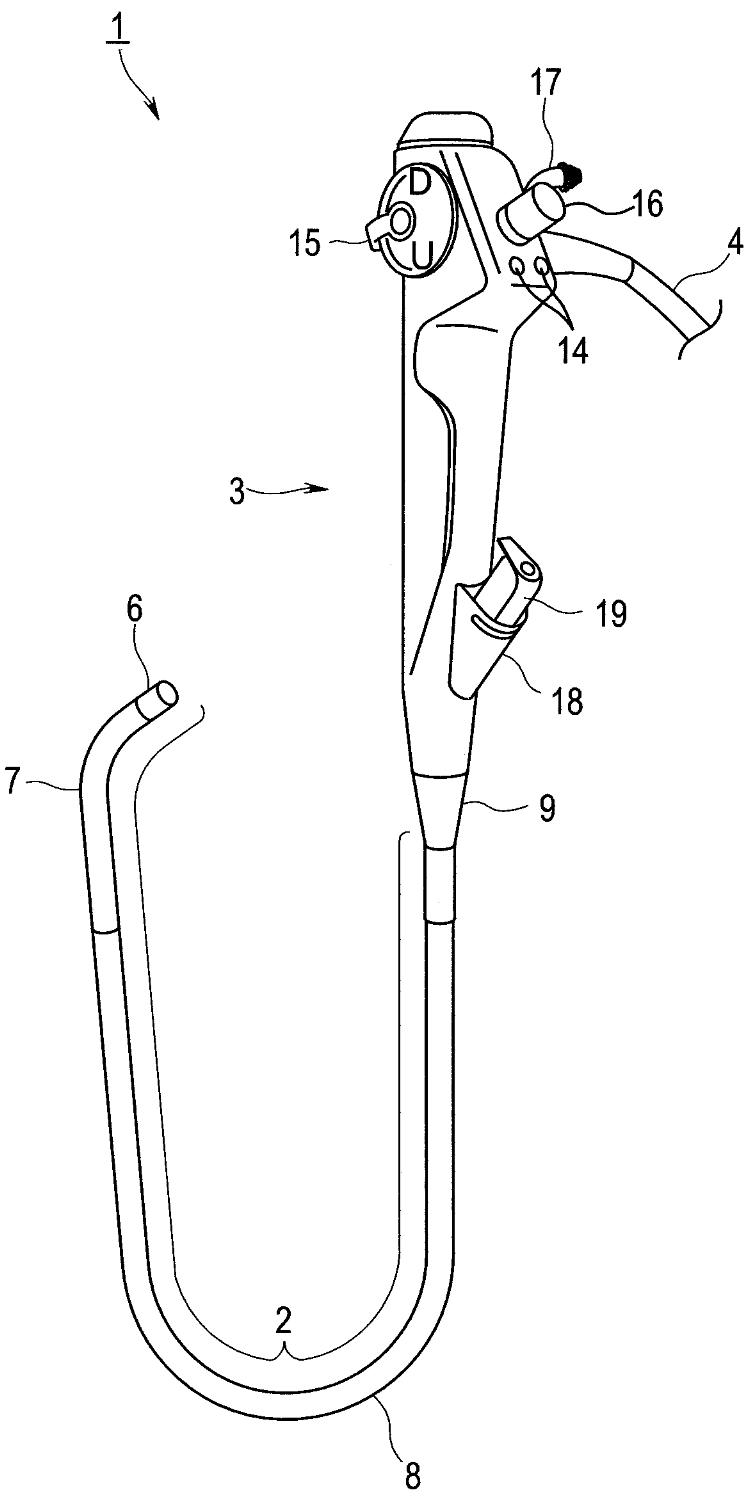
FIG. 1 is a partial perspective view showing an endoscope of an embodiment where a bending portion is provided in an insertion portion.

As shown in FIG. 1, an endoscope 1 is configured to include an endoscope insertion portion (hereinafter simply referred to as "insertion portion") 2, an operation portion 3, and a universal cord 4, the insertion portion 2 having an elongated flexible tube shape, the operation portion 3 being provided on a proximal end side of the insertion portion 2, the universal cord 4 extending from the operation portion 3. An endoscope connector connected to an image processing device, a light source device, or other device is provided on an extension end of the universal cord 4 (neither shown in the drawing).

For the purpose of preventing infection, reducing costs, or the like, it is preferable that the endoscope 1 be a disposable single-use endoscope that is disposed after use (used once). However, needless to say, the endoscope 1 may be a reusable product that is reused after being subjected to disinfection and sterilization treatment.

A main part of the insertion portion 2 includes, in order from a distal end side, a rigid distal end portion 6, a bending portion 7, and a soft flexible tube portion 8. The distal end portion 6 includes an observation optical system not shown in the drawing in the inside thereof, for example. The bending portion 7 is an active bending portion that is continuously provided on a proximal end side of the distal end portion 6, and is actively bendable in a plurality of directions, for example, two directions including an upward direction and a downward direction (U/D). The flexible tube portion 8 is continuously provided on a proximal end side of the bending portion 7 and has flexibility.

The bending portion 7 is bent in either one of the upward direction or the downward direction with an operation of a bending operation lever 15 provided on the operation portion 3. The bending portion 7 may be configured to be bendable in two directions including a leftward direction and a rightward direction (L/R), may be configured to be bendable in four directions including the upward direction, the downward direction, the leftward direction, and the rightward direction, or may be configured to be bendable in a composite direction of the upward direction, the downward direction, the leftward direction, and the rightward direction. The endoscope 1 may be configured to be provided with a passive bending portion that is continuously provided on the proximal end side of the bending portion 7.

The operation portion 3 is provided with remote switches 14, a suction button 16, and a suction pipe sleeve 17, for example. The remote switches 14 are provided, for example, for instructing to perform image control, such as freezing or releasing. The suction button 16 is provided for performing a suction operation. The suction pipe sleeve 17 communicates with a suction channel not shown in the drawing provided in the insertion portion 2. The operation portion 3 is also provided with a treatment instrument insertion port 18 for insertion of a treatment instrument, such as forceps, into the suction channel. A forceps plug 19 is mounted on the treatment instrument insertion port 18.

Figure 2:
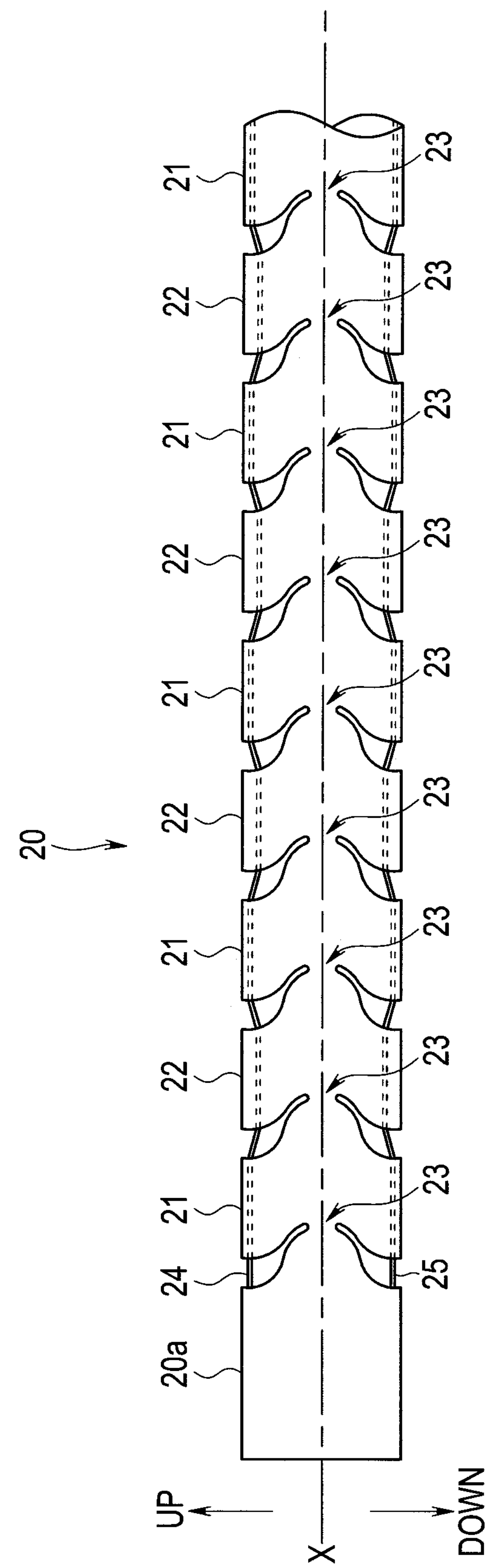
FIG. 2 is a side view showing a configuration of a bending tube provided in the bending portion of the insertion portion of the endoscope of the embodiment.

As shown in FIG. 2, in the present embodiment, a bending tube 20 having a substantially cylindrical shape is provided in the bending portion 7. An outer periphery of the bending tube 20 is covered by a braid, being a mesh-like tube, and bending rubber. However, the braid and the bending rubber are omitted in FIG. 2 for the sake of simplifying the drawing.

The bending tube 20 includes a distalmost-end bending piece 20*a* connected to a distal end rigid portion (not shown in the drawing) of a distal end frame (distal end forming portion), which forms the distal end portion 6 of the insertion portion 2. The bending tube 20 is configured to include first bending pieces 21, being a plurality of first joint rings, and second bending pieces 22, being a plurality of second joint rings, the first bending pieces 21 and the second bending pieces 22 being continuously provided on a proximal end side of the distalmost-end bending piece 20*a*.

The first bending pieces 21 and the second bending pieces 22 are alternately arranged in a direction of a longitudinal axis X in which the bending portion 7 forms a straight line. The distalmost-end bending piece 20*a*, the first bending pieces 21, and the second bending pieces 22 are coupled with each other by coupling portions 23, the first bending pieces 21 and the second bending pieces 22 being alternately disposed, the coupling portions 23 forming rotation support portions at two portions, that is, both side portions in a left-and-right direction of each of the first bending pieces 21 and the second bending pieces 22.

The bending tube 20 is formed of a synthetic resin by injection molding such that the distalmost-end bending piece 20*a*, the plurality of first bending pieces 21, and the plurality of second bending pieces 22 are integrally and continuously provided via the coupling portions 23. The number of first bending pieces 21 and the number of second bending pieces 22 are suitably determined according to an entire length of the bending portion 7. The bending tube 20 may be connected to a flexible tube 8 via a passive bending portion, being another bending tube that is bent only by a force from the outside. In such a case, a structure is adopted where a connection part (not shown in the drawing) is attached to a proximal end side (last piece) of the bending tube 20 so as to allow the bending tube 20 to be connected to the passive bending portion.

Figure 3:
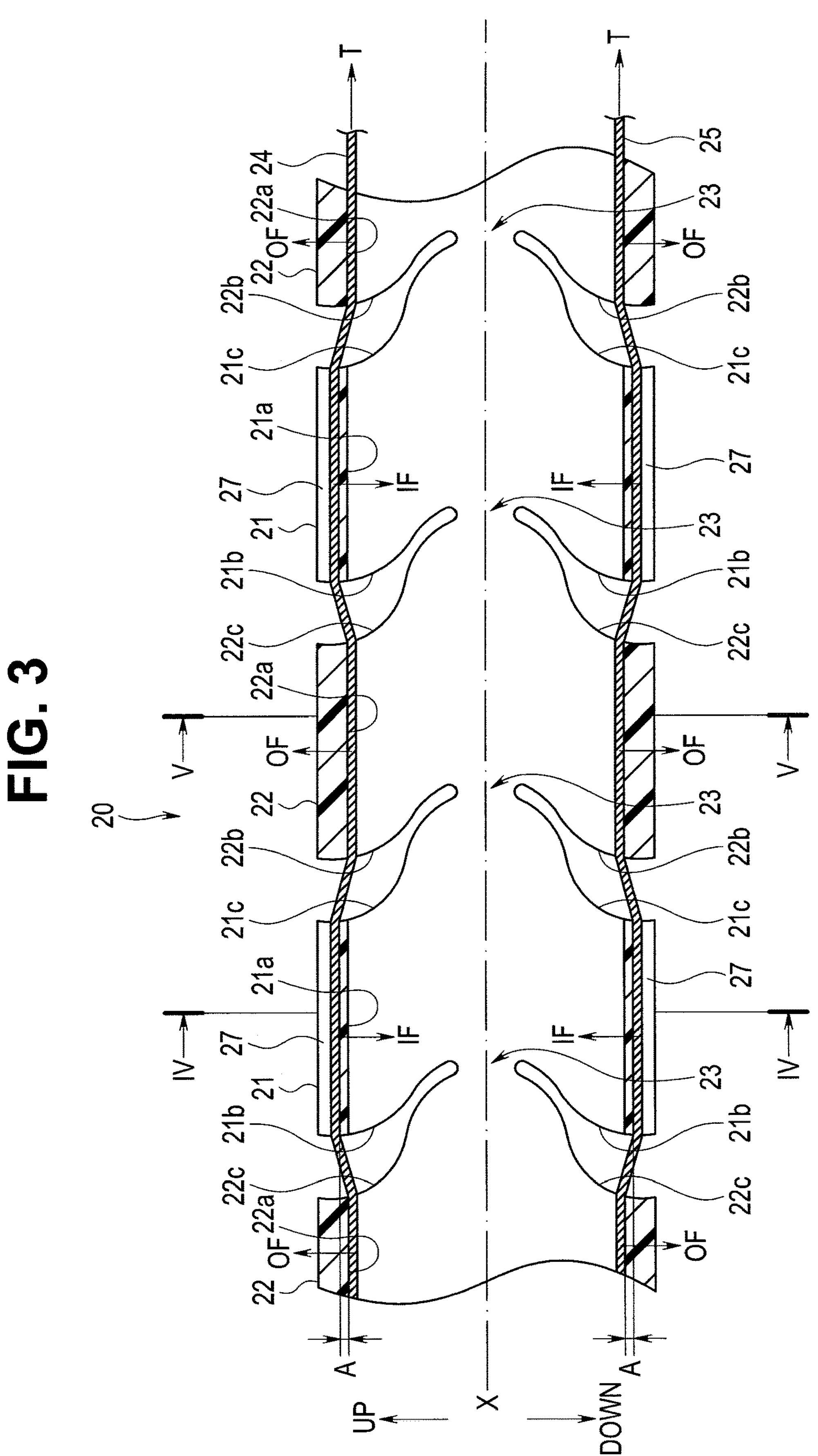
FIG. 3 is a partial cross-sectional view showing the configuration of the bending tube of the endoscope of the embodiment.
Figure 4:
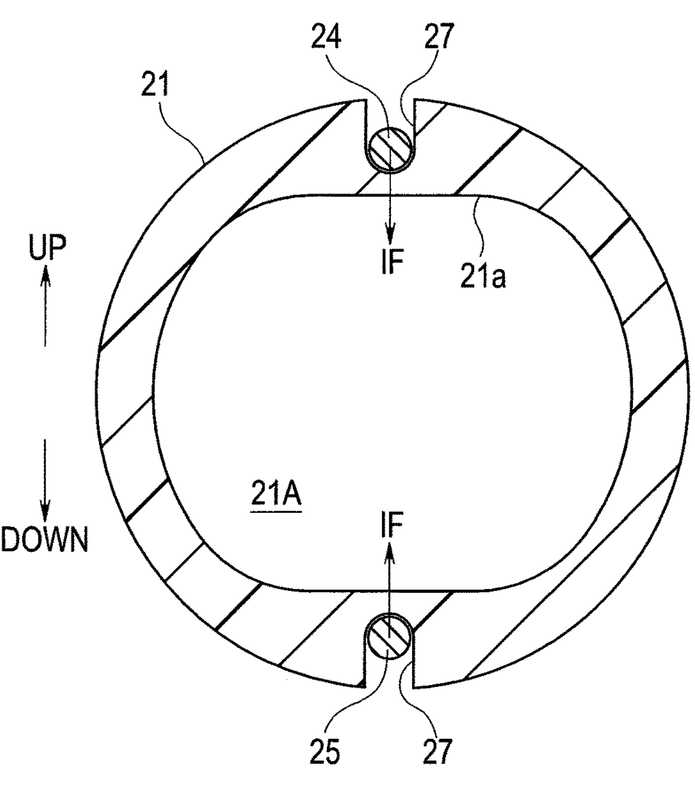
FIG. 4 is a cross-sectional view showing a configuration of a first bending piece of the bending tube of the endoscope of the embodiment invention taken along line IV-IV in FIG. 3.
Figure 5:
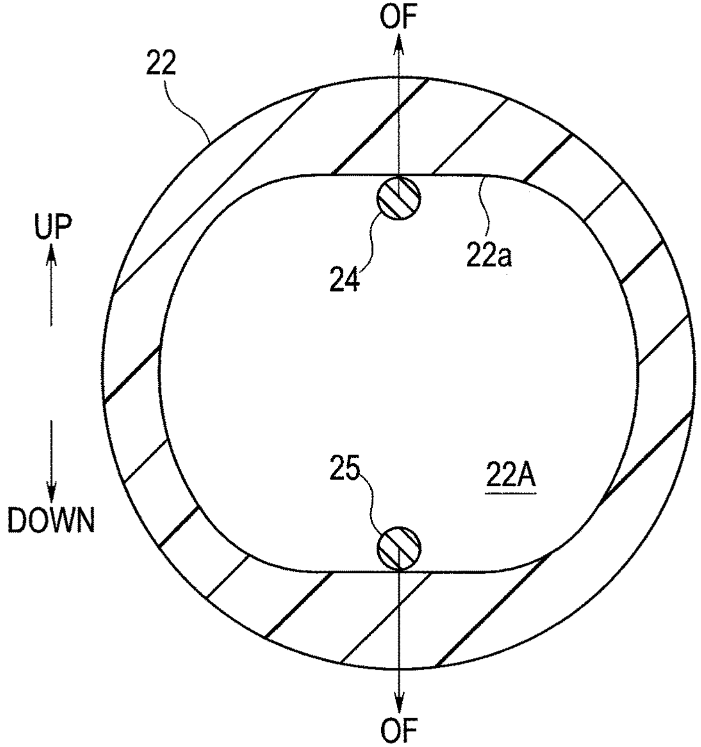
FIG. 5 is a cross-sectional view showing a configuration of a second bending piece of the bending tube of the endoscope of the embodiment taken along line V-V in FIG. 3.

As shown in FIG. 3 to FIG. 5, each first bending piece 21 and each second bending piece 22 has an annular shape, and the first bending piece 21 has an inner surface 21*a* and the second bending piece 22 has an inner surface 22*a* so as to allow various internal components, such as a light guide and an image pickup cable, to be inserted through the first bending piece 21 and the second bending piece 22.

In the present embodiment, the first bending piece 21 has a distal end surface 21*b* and a proximal end surface 21*c* each of which has a predetermined curved surface shape. The first bending piece 21 has grooves 27 on an outer peripheral portion over an entire length at upper and lower portions in an up-and-down direction, the grooves 27 serving as wire guide portions extending along the longitudinal axis X. In the present embodiment, the second bending piece 22 also has a distal end surface 22*b* and a proximal end surface 22*c* each of which has a predetermined curved shape.

The distal end surface 22*b* of each second bending piece 22 is brought into contact with the proximal end surface 21*c* of each first bending piece 21, so that an angle at which the bending tube 20 of the bending portion 7 is bent at maximum is defined.

Bending operation wires 24, 25 are disposed in the bending tube 20, the bending operation wires 24, 25 being two traction members that causes the respective first bending pieces 21 and the respective second bending pieces 22 to rotate. When two bending operation wires 24, 25 are pulled or loosened, each coupling portion 23 that couples the first bending piece 21 with the second bending piece 22 is deformed, thus forming a rotation fulcrum, so that the bending tube 20 is bent in either of two directions, the upward direction or the downward direction (U/D).

In other words, the bending tube 20 has a rivetless configuration where the first bending pieces 21 and the second bending pieces 22 are not connected by rivets or the like.

The two bending operation wires 24, 25 are caused to extend along an outer peripheral side of each first bending piece 21 in a state of being accommodated in the grooves 27 of the first bending piece 21, and are caused to pass through an inner peripheral side being the inside of each second bending piece 22.

Specifically, the bending operation wire 24 is disposed in the groove 27 of each first bending piece 21 in the direction of the longitudinal axis X, the groove 27 being located at the upper position in the upward direction (U). The bending operation wire 25 is disposed in the groove 27 of each first bending piece 21 in the direction of the longitudinal axis X, the groove 27 being located at the lower position in the downward direction (D). The bending operation wires 24, 25 are disposed in the inside of each second bending piece 22.

In other words, the bending operation wires 24, 25 are inserted through the first bending pieces 21 and the second bending pieces 22 such that the bending operation wires 24, 25 alternately lie along an outer side of each first bending piece 21 and an inner side of each second bending piece 22. When the bending operation wires 24, 25 are inserted through the first bending pieces 21 and the second bending pieces 22, the bending operation wires 24, 25 in the second bending piece 22 are pulled out from gaps by tweezers or the like, each gap being formed between the proximal end surface 21*c* of the first bending piece 21 and the distal end surface 22*b* of the second bending piece 22 which face each other.

The bending operation wires 24, 25 which are pulled out from the gaps are caused to extend along the grooves 27 formed on the outer peripheral portion of the adjacent first bending piece 21, and are then inserted through the inside of another adjacent second bending piece 22. By repeating such a procedure, the bending operation wires 24, 25 are caused to alternately be positioned along the inner wall and the outer side (the grooves 27) of the pieces.

Distal ends of the bending operation wires 24, 25 are joined to a distal end rigid portion (not shown in the drawing) by welding or the like, the distal end rigid portion being fitted in the distalmost-end bending piece 20*a*. Proximal ends of the bending operation wires 24, 25 are connected to a rotating mechanism, such as a pulley or a sprocket, which is rotated by the bending operation lever 15.

In the bending tube 20 having the above-mentioned configuration, when a predetermined tension T toward a proximal end side is applied to the bending operation wires 24, 25 as shown in FIG. 3, a stress IF from the outside toward the inside is generated in each first bending piece 21 and a stress OF from the inside toward the outside is generated in each second bending piece 22.

In other words, each of the bending operation wires 24, 25 is inserted through the first bending pieces 21 and the second bending pieces 22 such that each of the bending operation wires 24, 25 comes into contact with the groove 27 of each first bending piece 21 and the inner surface 22*a*, being the inner wall, of each second bending piece 22, thus being disposed at different positions in a direction orthogonal to the longitudinal axis X.

Specifically, as shown in FIG. 4 and FIG. 5, each first bending piece 21 has a hole portion 21A formed by the inner surface 21*a*, each second bending piece 22 has a hole portion 22A formed by the inner surface 22*a*, and the hole portion 21A and the hole portion 22A are set to have the same cross-sectional shape. The same cross-sectional shape can include the substantially same cross-sectional shape. Therefore, stepped portions are formed, each stepped portion having a wall thickness (A) ranging from the groove 27 of each first bending piece 21 to the inner surface 22*a* of each second bending piece 22 (see FIG. 3).

Accordingly, since each of the bending operation wires 24, 25 is inserted through the inside of the adjacent second bending piece 22 from the outer side of the first bending piece 21, when the tension T toward the proximal end side is applied, each of the bending operation wires 24, 25 comes into contact with each first bending piece 21, thus generating the stress IF in each first bending piece 21, and comes into contact with each second bending piece 22, thus generating the stress OF, the stress IF being a pushing force that contracts each first bending piece 21 inward, the stress OF being a pushing force that causes each second bending piece 22 to expand outward.

Therefore, the bending operation wires 24, 25 push down the grooves 27 of each first bending piece 21 inward, and lift the inner wall being the inner surface 22*a* of each second bending piece 22 outward. In other words, the respective grooves 27 formed on the outer peripheral surface of each first bending piece 21 form first contact portions with which the bending operation wires 24, 25 come into contact, and wall portions of each inner surface 22*a*, being an inner peripheral surface of each second bending piece 22, form second contact portions with which the bending operation wires 24, 25 come into contact.

With such a configuration of the bending tube 20, when the tension T is applied to the bending operation wires 24, 25, so that the bending operation wires 24, 25 come into contact with the first bending pieces 21 and the second bending pieces 22, the stress IF toward the inside is generated in each first bending piece 21 and the stress OF toward the outside is generated in each second bending piece 22. Accordingly, twisting of each first bending piece 21 and twisting of each second bending piece 22 are suppressed and hence, it is possible to achieve a structure that is resistant against twisting.

Figure 6:
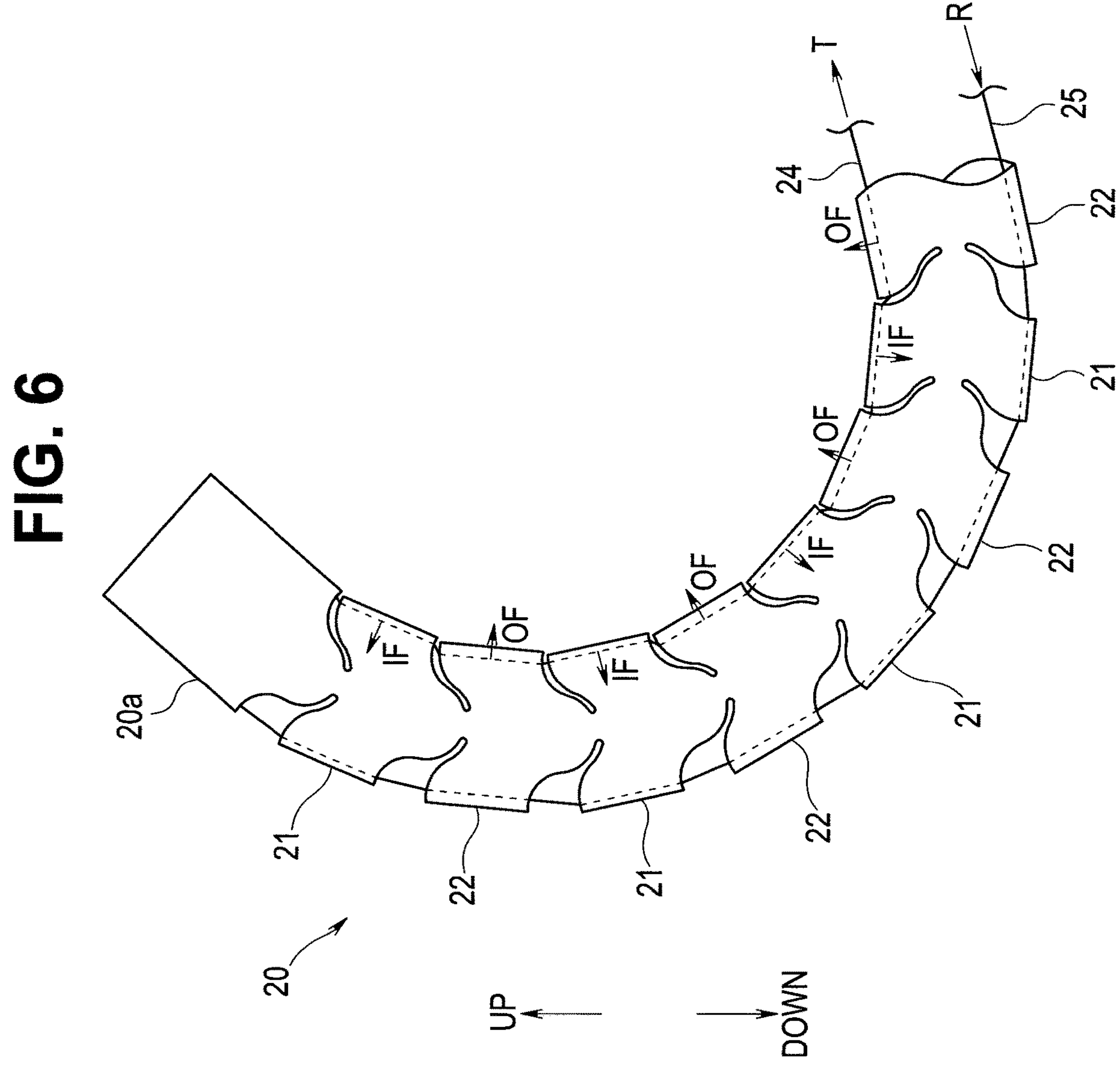
FIG. 6 is a side view partially showing a state where the bending tube of the endoscope of the embodiment is bent upward.

In the present embodiment, also in a state where the bending tube 20 is bent in the upward direction (UP) as shown in FIG. 6, the stress IF is applied to each first bending piece 21 from the pulled bending operation wire 24 which is disposed on the upper side and the stress OF is applied to each second bending piece 22. With such a configuration, twisting of each first bending piece 21 and twisting of each second bending piece 22 are suppressed and hence, the bending tube 20 can achieve a structure that is resistant against twisting. The bending operation wire 25 which is disposed on the lower side is loosened, thus being in a state where the bending operation wire 25 is released from the tension T and a loosening pushing force R is generated.

Also, in a state where the bending tube 20 is bent in the downward direction (DOWN), the same action occurs, so that the stress IF is applied to each first bending piece 21 from the pulled bending operation wire 25 disposed on the lower side and the stress OF is applied to each second bending piece 22. With such a configuration, twisting of each first bending piece 21 and twisting of each second bending piece 22 are suppressed and hence, the bending tube 20 can achieve a structure that is resistant against twisting. Further, in such a state, the bending operation wire 24 which is disposed on the upper side is loosened, thus being in a state where the bending operation wire 24 is released from the tension T and a loosening pushing force (R) is generated.

Figure 7:
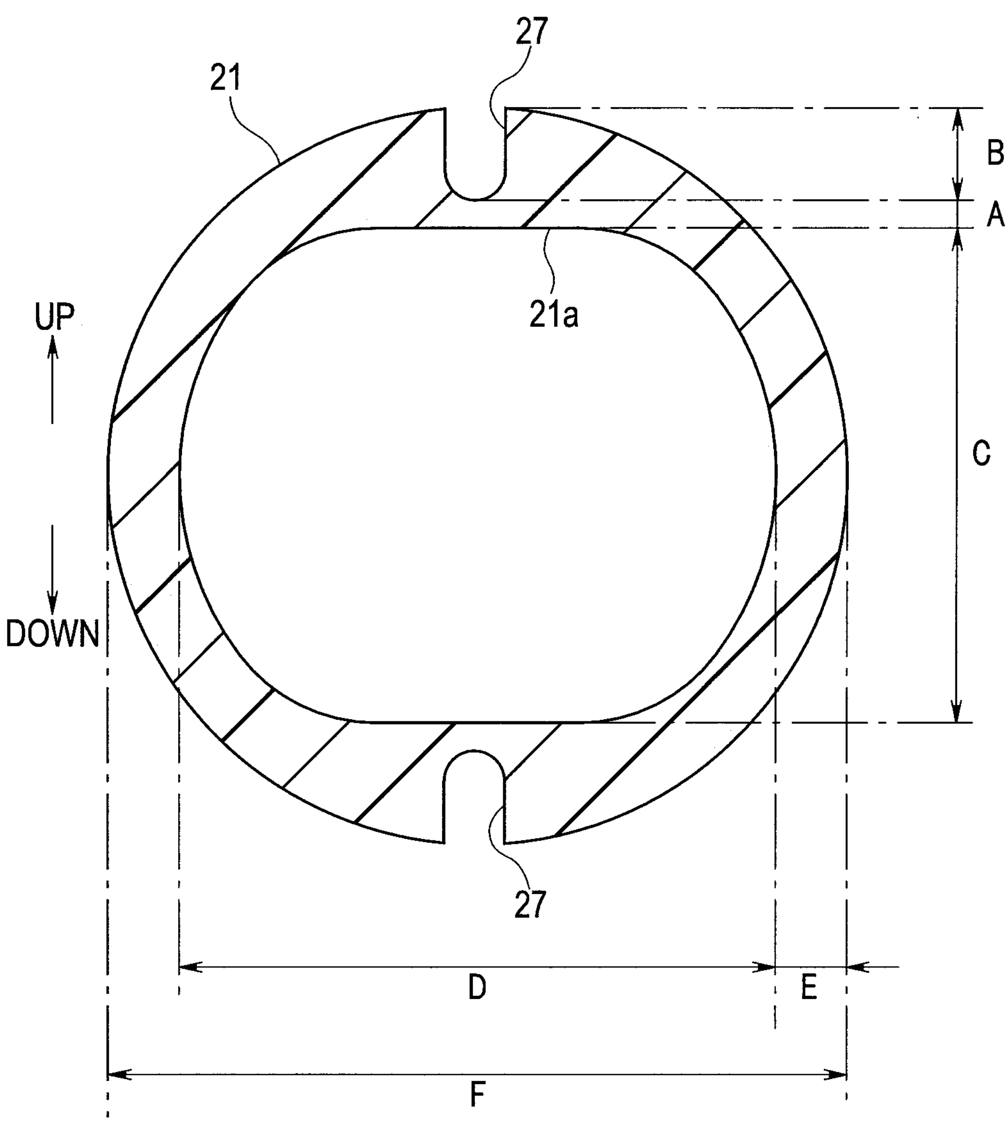
FIG. 7 is a cross-sectional view showing a dimensional relationship of the first bending piece of the endoscope of the embodiment.

The dimensional relationship of the first bending piece 21 will be described. As shown in FIG. 7, for example, assume that a wall thickness of a thinnest portion of the first bending piece 21, that is, a wall thickness from the groove 27 to the inner surface 21*a*, is taken as A, a depth of the groove 27 in which the bending operation wires 24, 25 are disposed is taken as B, a minor axis, in the present embodiment, a dimension in the up-and-down direction of the hole portion 21A, being an inner space, is taken as C, a major axis, that is, a dimension in the left-and-right direction of the hole portion 21A is taken as D, and a wall thickness in a direction in the major axis is taken as E. In such a case, an outer diameter F, the wall thickness E, and inner dimensions D, C can be defined by the following equation 1 to expression 3.

$$F=D+2E \qquad \text{equation 1}$$

$$E<(B+A) \qquad \text{expression 2}$$

$$D>C \qquad \text{expression 3}$$

The depth B of the groove 27 can be defined by the following expression 4 based on equation 1 and expression 2.

$$B>(F-D-2A)/2 \qquad \text{expression 4}$$

The dimension C of the minor axis can be defined by the following expression 5 based on equation 1 and expression 3.

$$C<F-2E \qquad \text{expression 5}$$

When D=3 mm, E=0.5 mm, F=4 mm, and A=0.1 mm are set, for example, the depth B of the groove 27 satisfies B>0.4 mm and the dimension C of the minor axis satisfies C<3 mm based on the above-mentioned equation 1 to expression 5.

When D=3 mm, E=0.2 mm, F=3.4 mm, and A=0.1 mm are set, for example, the depth B of the groove 27 satisfies B>0.1 mm and the dimension C of the minor axis satisfies C<3 mm.

Figure 8:
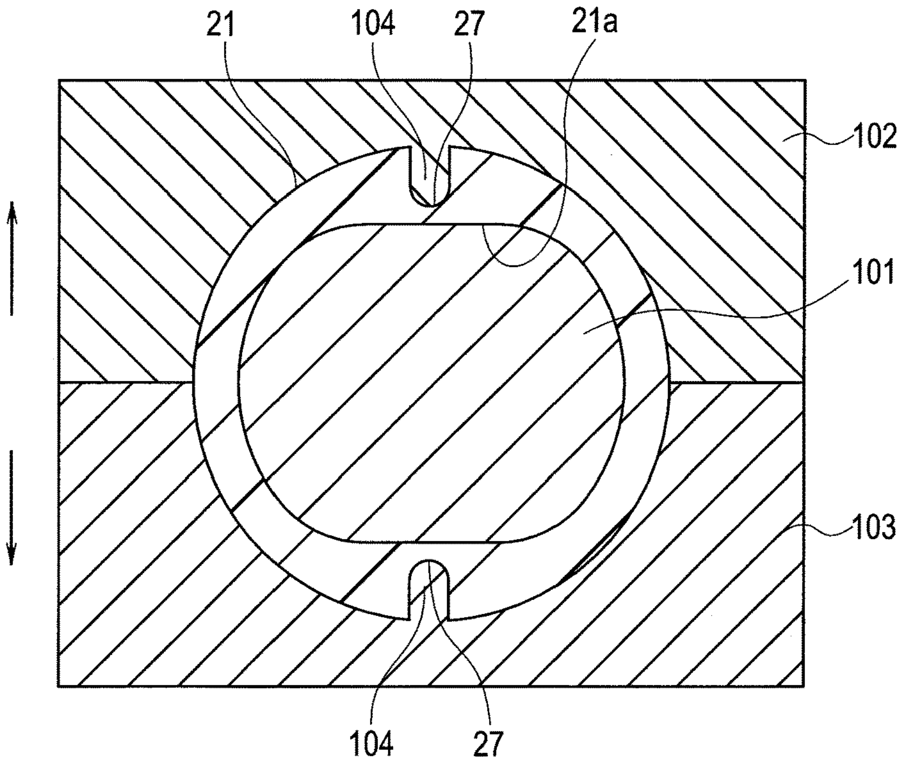
FIG. 8 is a cross-sectional view showing a portion of a mold used for forming the first bending piece of the endoscope of the embodiment by injection molding.
Figure 9:
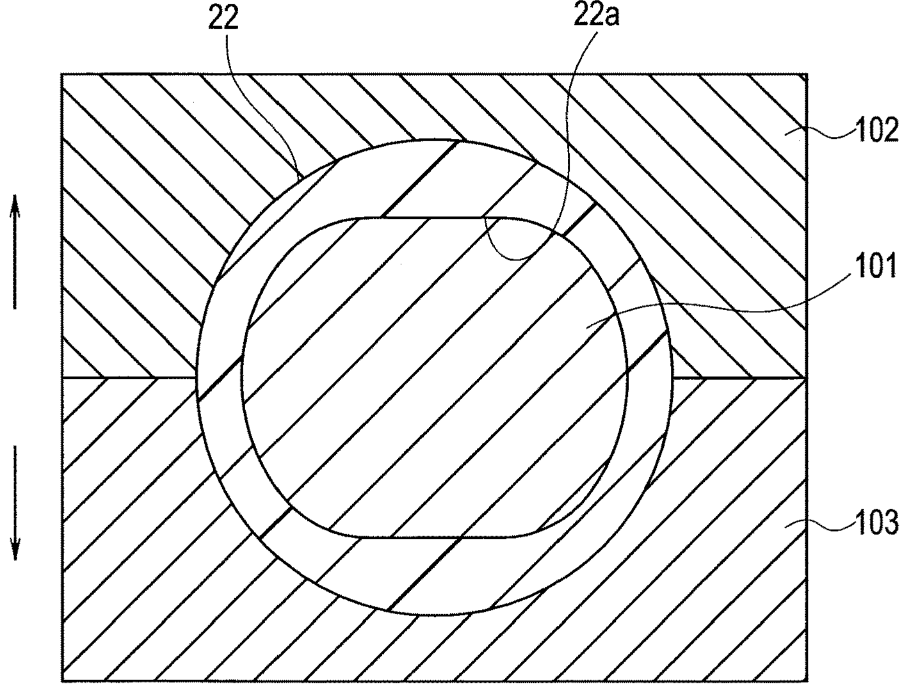
FIG. 9 is a cross-sectional view showing a portion of the mold used for forming the second bending piece of the endoscope of the embodiment by injection molding.

Hereinafter, the description will be made for a mold used in forming the bending tube 20 by injection molding. As shown in FIG. 8 and FIG. 9, in the bending tube 20, each first bending piece 21 has the hole portion 21A, forming the inner space, each second bending piece 22 has the hole portion 22A, forming the inner space, and the hole portion 21A and the hole portion 22A have the same cross-sectional shape. The same cross-sectional shape can include the substantially same cross-sectional shape. Therefore, it is possible to use an inner mold having the same outer shape for an inner mold 101 of the mold used for molding the hole portion 21A of each first bending piece 21 and the hole portion 22A of each second bending piece 22.

For an external shape of the bending tube 20, a first outer mold 102 and a second outer mold 103 of the mold are used, the first outer mold 102 and the second outer mold 103 being obtained by dividing the mold into two portions in the up-and-down direction, the first outer mold 102 and the second outer mold 103 forming the same cross-sectional shape as the external shape of the bending tube 20. The same cross-sectional shape can include the substantially same cross-sectional shape. When the first outer mold 102 is opened in the upward direction (UP) indicated by an arrow and the second outer mold 103 is opened in the downward direction (DOWN) indicated by an arrow, the molded bending tube 20 is removed from the mold.

For each first bending piece 21, the grooves 27 are mold. The bending operation wires 24, 25 are disposed in the grooves 27. Therefore, each of a portion of the first outer mold 102 corresponding to the first bending piece 21 and a portion of the second outer mold 103 corresponding to the first bending piece 21 has a shape that includes a protruding portion 104 for molding the groove 27 in cross section.

Further, gaps are formed between each first bending piece 21 and each second bending piece 22 to achieve a desired curved shape and hence, each of the first outer mold 102 and the second outer mold 103 includes protrusions not shown in the drawing for the entire length of the bending tube 20, the protrusions being used for molding the gaps.

Figure 10:
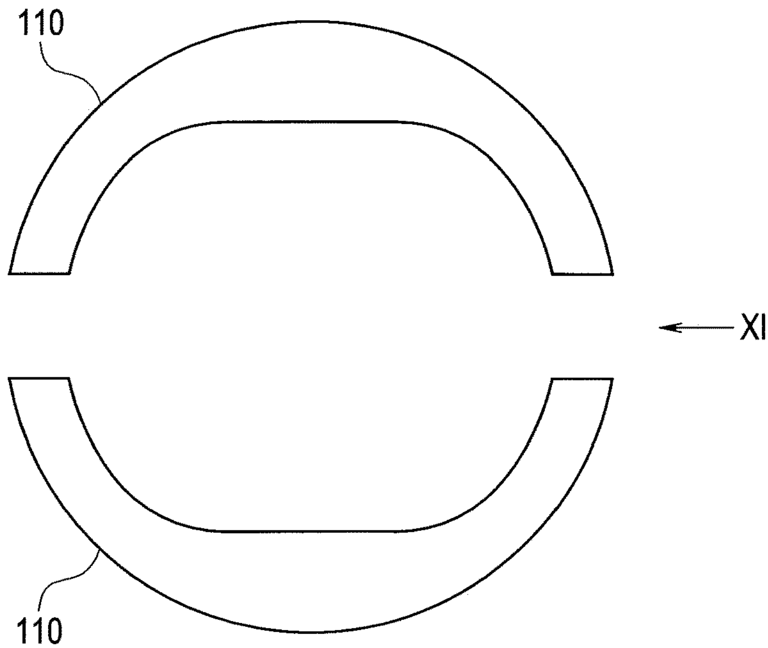
FIG. 10 is a front view showing inner molds used for forming gaps for the endoscope of the embodiment.
Figure 11:
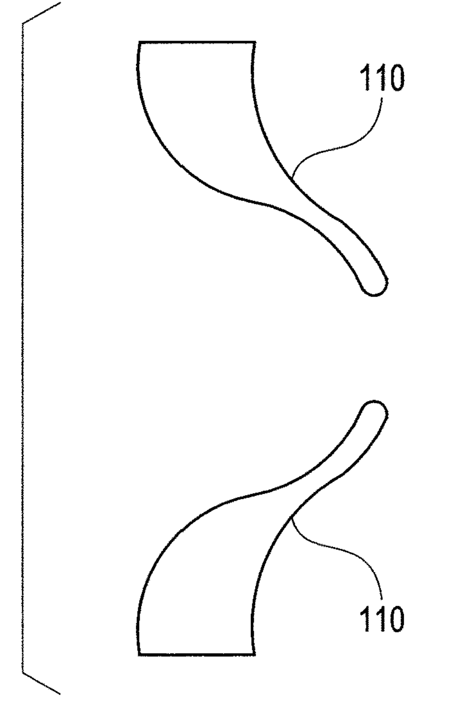
FIG. 11 is a side view showing the inner molds used for forming the gaps for the endoscope of the embodiment as viewed in a direction indicated by an arrow XI in FIG. 10.

A plurality of gaps is formed between each first bending pieces 21 and each second bending pieces 22 to achieve a desired curved shape. In other words, a plurality of portions shown in FIG. 3 are provided which are obtained by partially reducing the wall thickness of the bending tube 20, each of the portions being formed by the proximal end surface 21*c* of the first bending piece 21, the distal end surface 22*b* of the second bending piece 22, and the coupling portion 23. Therefore, the mold includes inner molds 110 shown in FIG. 10 and FIG. 11 used for molding the plurality of gaps in addition to the first outer mold 102, the second outer mold 103, and the inner mold 101, the number of inner molds 110 corresponding to the number of gaps.

Figure 12:
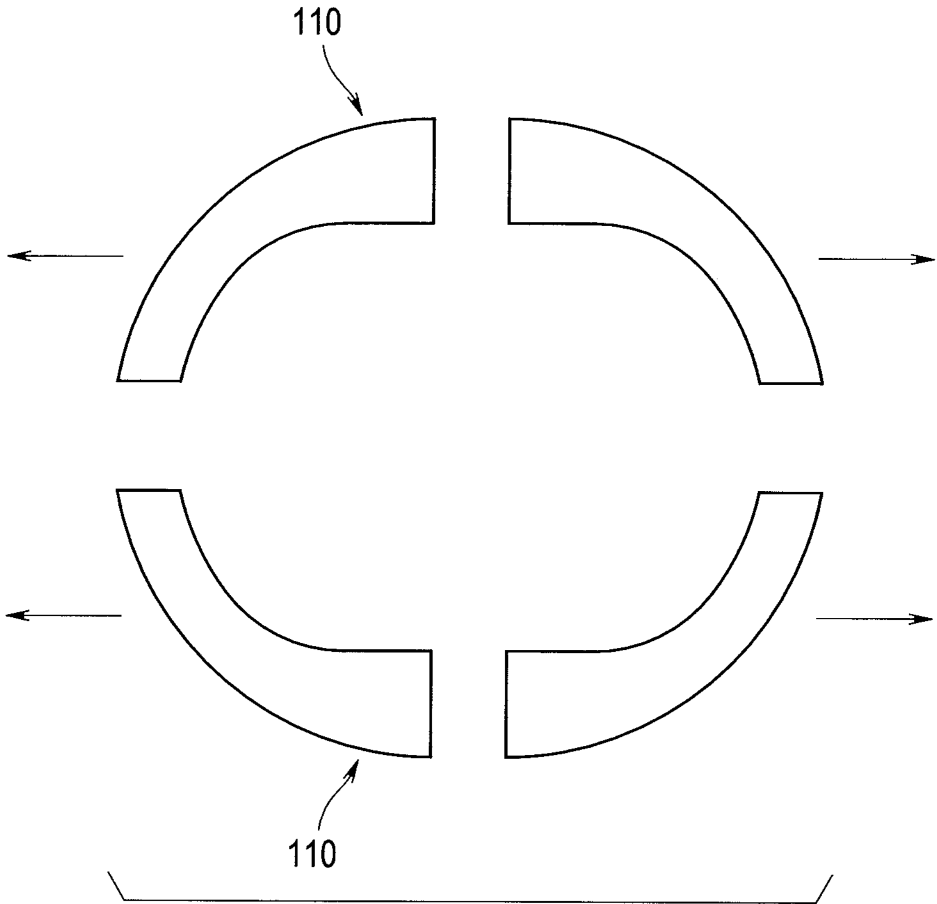
FIG. 12 is a front view showing inner molds for the endoscope of the embodiment, the inner molds being capable of being divided in a lateral direction from a center.

Each of these inner molds 110 has a shape that allows the inner molds 110 to be drawn in a vertical direction with respect to the arrows in FIG. 8, 9 (in the lateral direction) after the first outer mold 102 and the second outer mold 103 are opened in directions indicated by arrows in FIGS. 8 and 9 and the inner mold 101 is drawn in an axial direction. The plurality of inner molds 110 may be configured to be able to be divided in the lateral direction being a direction away from the center as shown in FIG. 12.

(First Modification)

Figure 13:
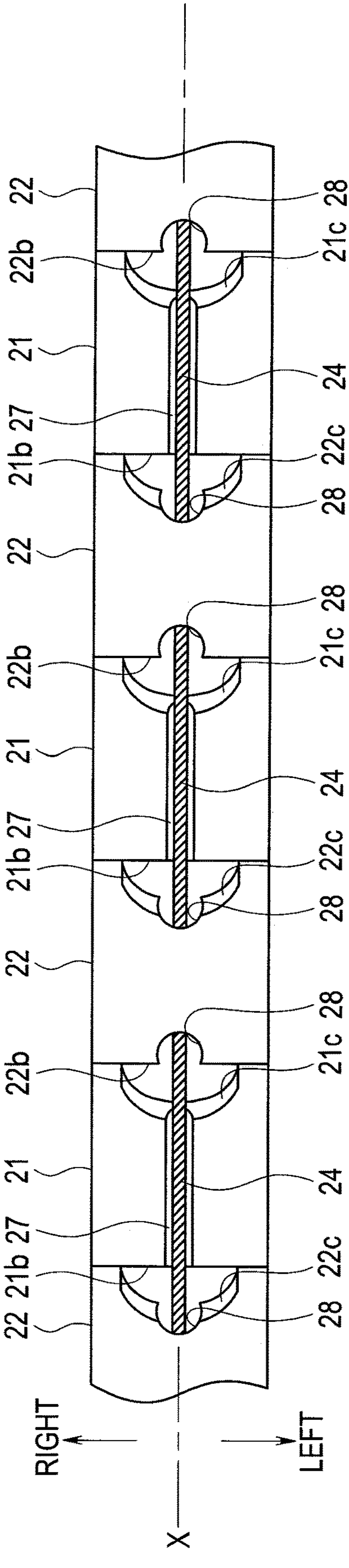
FIG. 13 is a top plan view showing a configuration of a bending tube of a first modification having recessed portions being wire escape holes.
Figure 14:
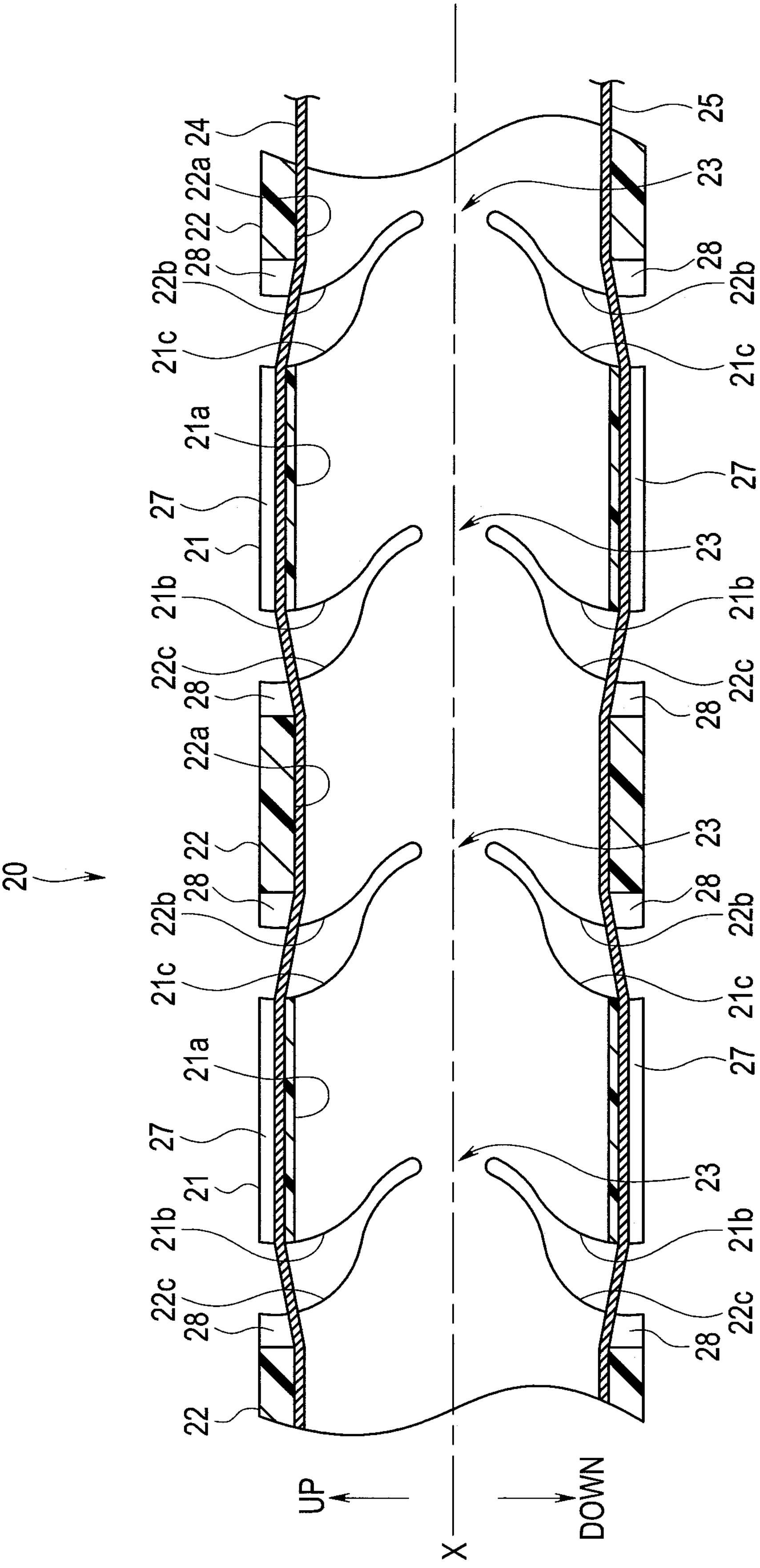
FIG. 14 is a cross-sectional view showing the configuration of the bending tube of the first modification having the recessed portions being the wire escape holes.

As shown in FIG. 13 and FIG. 14, to prevent the bending operation wires 24, 25 from being caught and bitten between the first bending piece 21 and the second bending piece 22 when the bending tube 20 is bent, a bending tube 20 of the present modification has recessed portions 28 at both upper and lower end portions of each second bending piece 22, the recessed portions 28 being wire escape holes for the bending operation wires 24, 25. By taking into account moldability of the bending tube 20, these recessed portions 28 are formed into a round hole shape by inserting pin-shaped round rods (not shown in the drawing) at both end portions of the second bending piece 22 where the bending operation wires 24, 25 pass.

Figure 15:
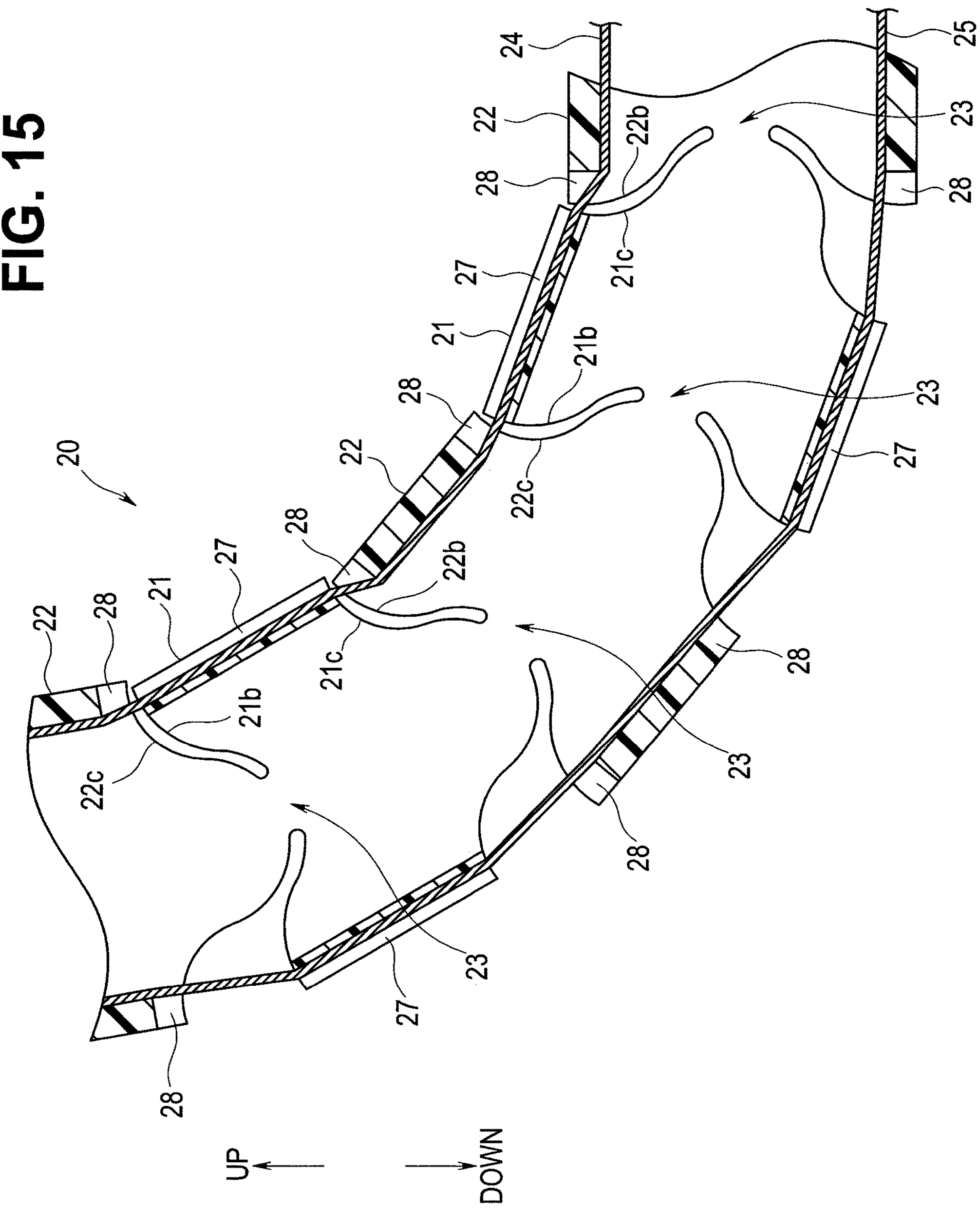
FIG. 15 is a partial cross-sectional view showing a state where the bending tube of the first modification having the recessed portions being the wire escape holes is bent upward.

As shown in FIG. 15, in a state where the bending tube 20 is bent, in the present modification, is bent upward, the bending operation wire 24 that is inserted through the inside of the second bending piece 22 from the groove 27 of the first bending piece 21 enters the recessed portion 28 of the second bending piece 22 and hence, it is possible to prevent the bending operation wire 24 from being caught and bitten between the distal end surface 21*b* of the first bending piece 21 and the proximal end surface 22*c* of the second bending piece 22 or between the proximal end surface 21*c* of the first bending piece 21 and the distal end surface 22*b* of the second bending piece 22.

Also in a state where the bending tube 20 is bent downward, in the same manner, the bending operation wire 25 enters the recessed portion 28 of the second bending piece 22 and hence, it is possible to prevent the bending operation wire 25 from being caught and bitten between the distal end surface 21*b* of the first bending piece 21 and the proximal end surface 22*c* of the second bending piece 22 or between the proximal end surface 21*c* of the first bending piece 21 and the distal end surface 22*b* of the second bending piece 22.

Figure 16:
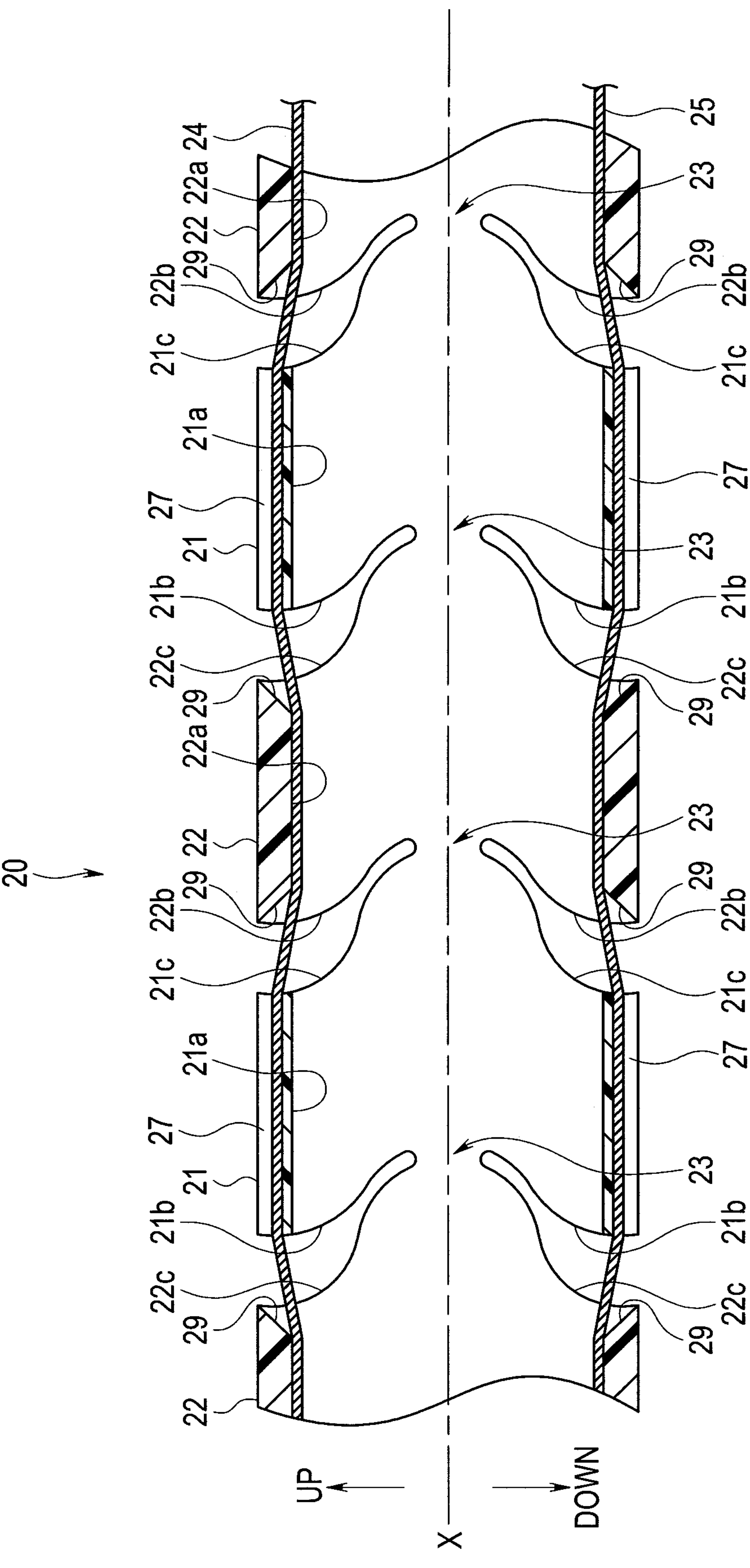
FIG. 16 is a cross-sectional view showing a configuration of a bending tube of the first modification having tapered surfaces serving as wire escape portions.
Figure 17:
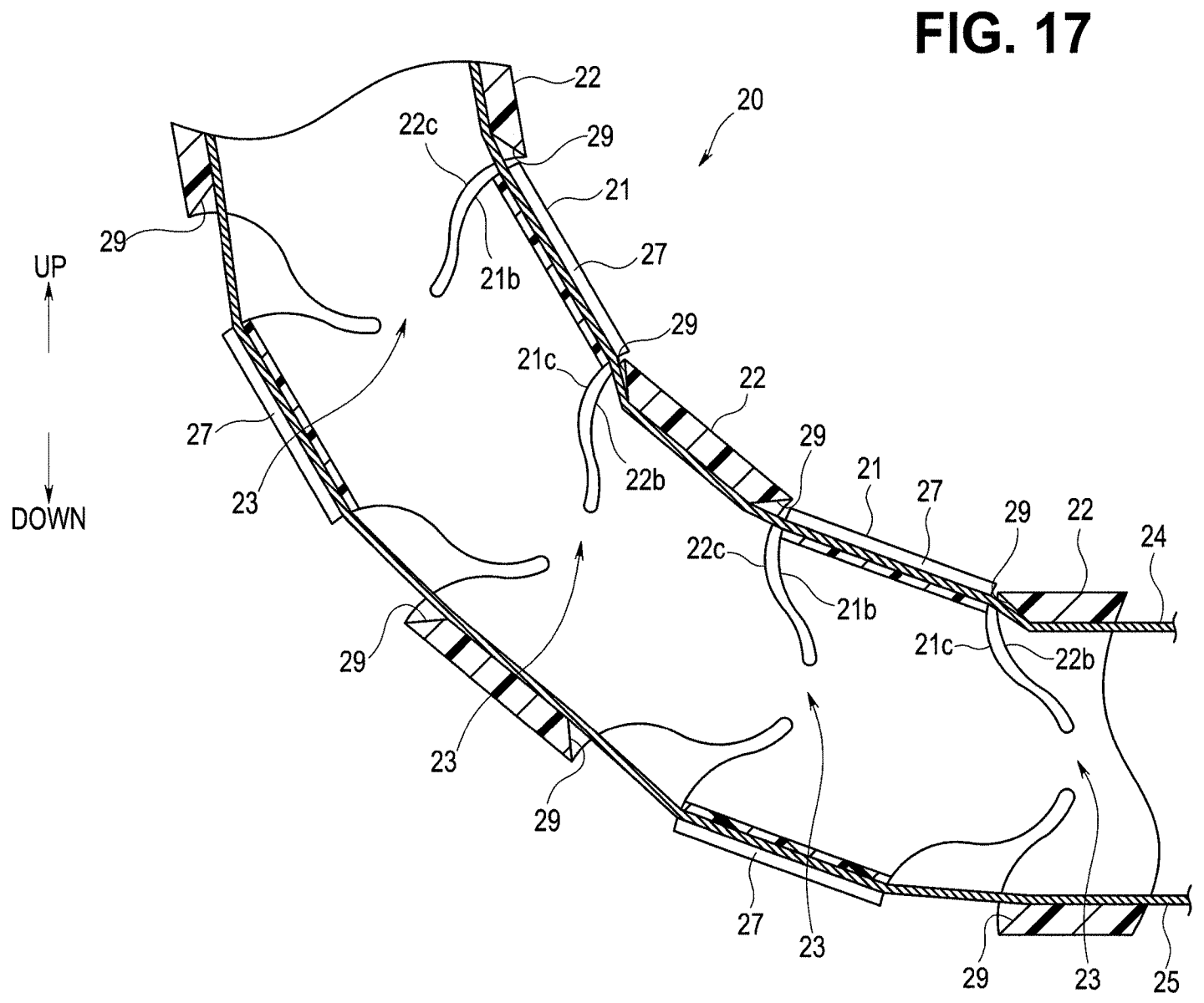

The configuration that prevents the bending operation wire 24 from being caught and bitten by the distal end surface 22*b* or the proximal end surface 22*c* of the second bending piece 22 as described above may be achieved by tapered surfaces 29 serving as wire escape portions formed by obliquely cutting away both upper and lower end portions of each second bending piece 22 as shown in FIG. 16 and FIG. 17.

The present modification shows, as an example, the configuration where each second bending piece 22 has the recessed portions 28 or the tapered surfaces 29. However, the configuration is not limited to the above, and each first bending piece 21 may have the recessed portions 28 or the tapered surfaces 29.

(Second Modification)

Figure 18:
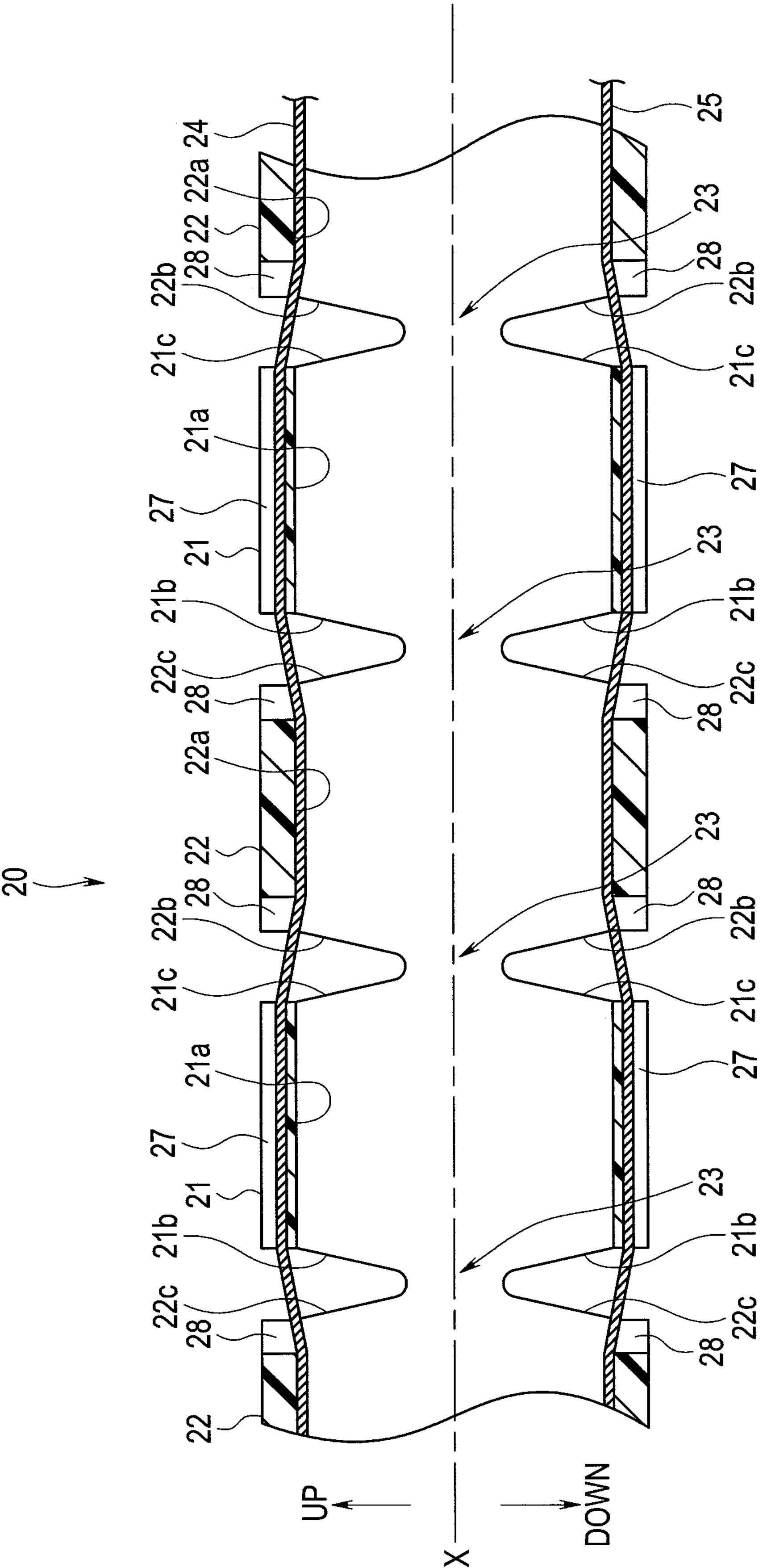
FIG. 18 is a cross-sectional view showing a configuration of a bending tube of a second modification.

In a bending tube 20 of the present modification, as shown in FIG. 18, a gap formed between the distal end surface 21*b* of each first bending piece 21 and the proximal end surface 22*c* of each second bending piece 22 and a gap formed between the proximal end surface 21*c* of each first bending piece 21 and the distal end surface 22*b* of the second bending piece 22 have a V shape. Even with such a configuration of the bending tube 20, it is possible to obtain the manner of operation and advantageous effects substantially equal to the manner of operation and advantageous effects of the above-mentioned embodiment and modification.

(Third Modification)

Figure 19:
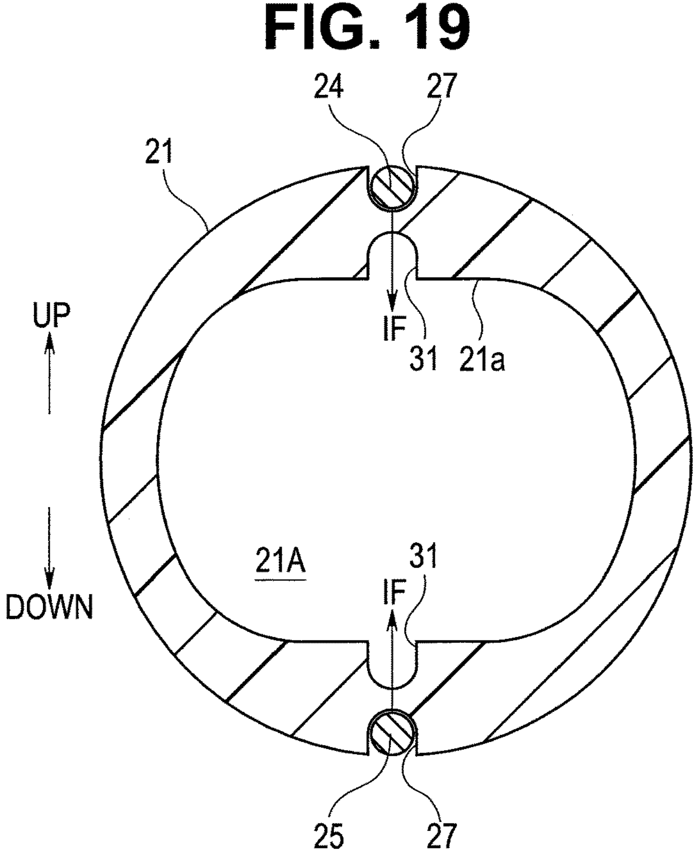
FIG. 19 is a cross-sectional view showing a configuration of a first bending piece of a bending tube of a third modification.
Figure 20:
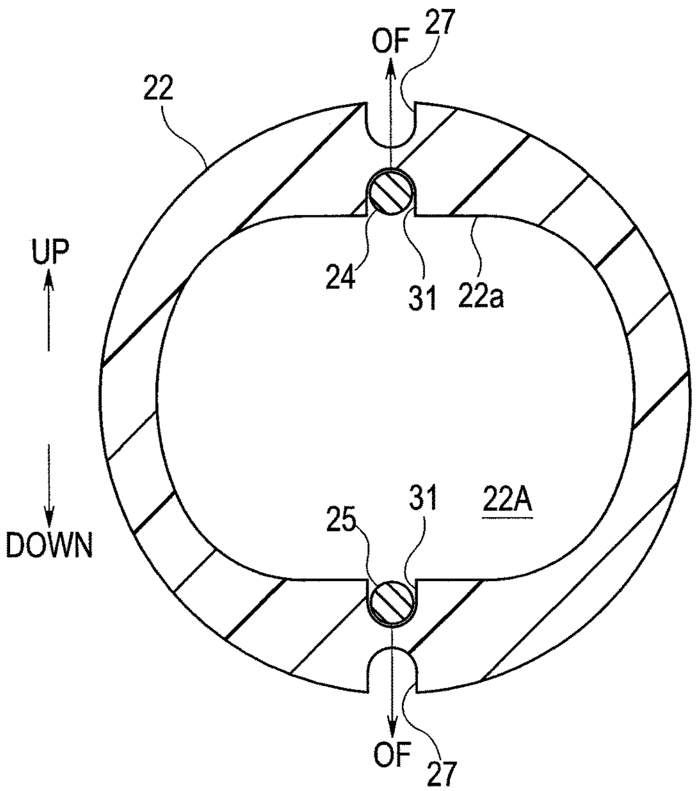
FIG. 20 is a cross-sectional view showing a configuration of a second bending piece of the bending tube of the third modification.

A bending tube 20 of the present modification has a configuration where, as shown in FIG. 19 and FIG. 20, each of the first bending piece 21 and the second bending piece 22 has the grooves 27, and grooves 31 are further provided on upper and lower inner walls in the up-and-down direction of each of the inner surfaces 21*a*, 22*a* over the entire length, the grooves 31 serving as wire guide portions that store the bending operation wires 24, 25 along the longitudinal axis X.

In the bending tube 20 having such a configuration, it is possible to dispose two bending operation wires 24, 25 along the grooves 31 formed on the inner surface 22*a* of each second bending piece 22. In other words, the bending operation wires 24, 25 are disposed along the grooves 27 formed on the outer side in each first bending piece 21, and the bending operation wires 24, 25 are disposed along the grooves 31 formed on the inner side in each second bending piece 22.

Figure 21:
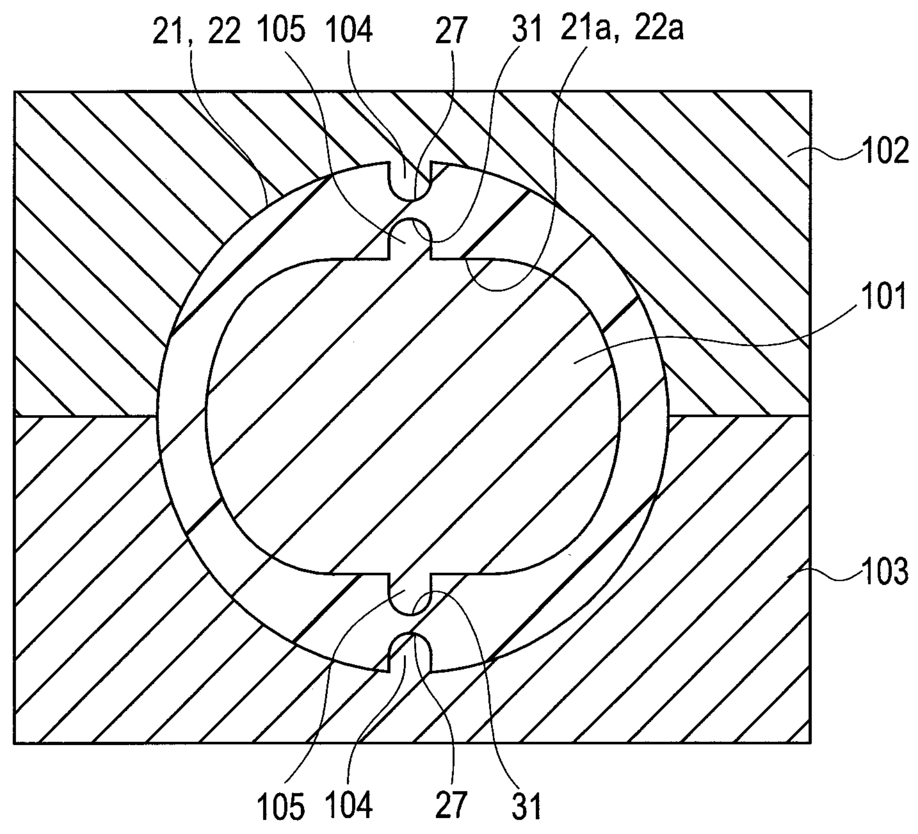
FIG. 21 is a cross-sectional view showing a portion of a mold used for forming the first bending piece and the second bending piece in the third modification by injection molding.

Therefore, in addition to the above-mentioned manner of operation and advantageous effects, the bending tube 20 can increase a space of the hole portion 22A into which internal components are accommodated, the hole portion 22A being an inner space of the second bending piece 22. Further, the bending operation wires 24, 25 are also fitted in the grooves 31 formed on the inner side of each second bending piece 22. Accordingly, positional displacement of the wires 24, 25 is suppressed and hence, it is possible to enhance an effect to suppress twisting. In addition to the above, the first bending piece 21 and the second bending piece 22 have the same shape in cross section orthogonal to the longitudinal axis X and hence, it is possible to manufacture the inner mold 101 and two kinds of outer molds, that is, the first outer mold 102 and the second outer mold 103 at a low cost, the inner mold 101, the first outer mold 102, and the second outer mold 103 forming a mold used for forming the bending tube 20 by injection molding as shown in FIG. 21. The same shape can include the substantially same shape.

Each of a portion of the first outer mold 102 corresponding to the first bending piece 21, a portion of the first outer mold 102 corresponding to the second bending piece 22, a portion of the second outer mold 103 corresponding to the first bending piece 21, and a portion of the second outer mold 103 corresponding to the second bending piece 22 has a cross-sectional shape that includes the protruding portion 104 for molding the groove 27. Each of a portion of the inner mold 101 corresponding to the first bending pieces 21 and a portion of the inner mold 101 corresponding to the second bending piece 22 has a cross-sectional shape that includes two protruding portions 105, that is, upper and lower protruding portions 105, for molding the grooves 31.

Figure 22:
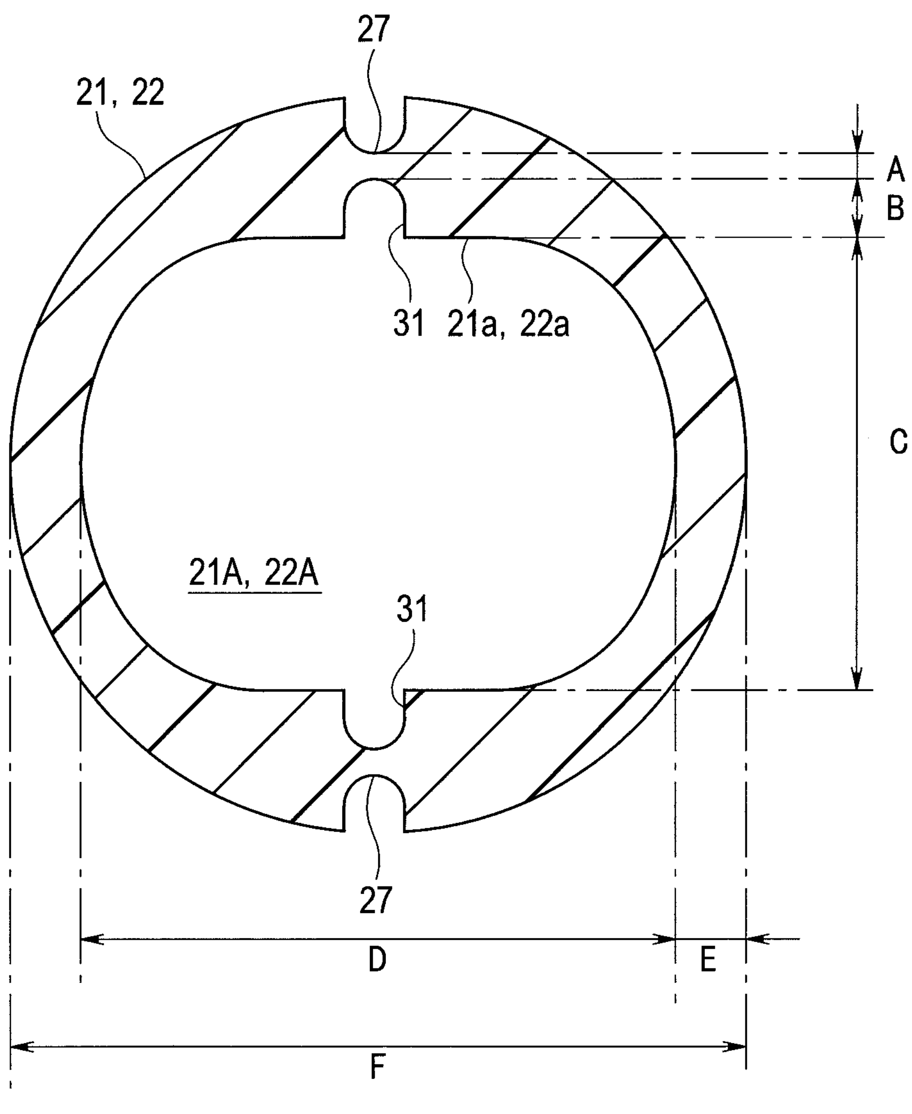
FIG. 22 is a cross-sectional view showing a dimensional relationship between the first bending piece and the second bending piece in the third modification.

The dimensional relationship of the first bending piece 21 and the second bending piece 22 will be described. As shown in FIG. 22, for example, assume that a wall thickness of a thinnest portion of the first bending piece 21 and the second bending piece 22, that is, a wall thickness from the groove 27 to the groove 31, is taken as A, a depth of the groove 31 which is formed on the inner side and in which the bending operation wires 24, 25 are disposed is taken as B, a minor axis, in the present modification, a dimension in the up-and-down direction of the hole portion 21A, 22A being an inner space, is taken as C, a major axis, that is, a dimension in the left-and-right direction of the hole portion 21A, 22A is taken as D, and a wall thickness in a direction in the major axis is taken as E. In such a case, the outer diameter F, the wall thickness E, and the inner dimensions D, C can be defined by the following equation 6 to expression 8.

$$F=D+2E \quad \text{equation 6}$$

$$E<(B+A) \quad \text{expression 7}$$

$$D>C \quad \text{expression 8}$$

The depth B of the groove 31 can be defined by the following expression 9 based on equation 6 and expression 7.

$$B>(F-D-2A)/2 \quad \text{expression 9}$$

The dimension C of the minor axis can be defined by the following expression 10 based on equation 6 and expression 8.

$$C<F-2E \quad \text{expression 10}$$

When D=3 mm, E=0.5 mm, F=4 mm, and A=0.1 mm are set, for example, the depth B of the groove 31 satisfies $B>0.2$ mm and the dimension C of the minor axis satisfies $C<3$ mm based on the above-mentioned equation 6 to expression 10. When D=3 mm, E=0.2 mm, F=3.4 mm, and A=0.1 mm are set, for example, the depth B of the groove 27 satisfies $B>0.75$ mm and the dimension C of the minor axis satisfies $C<3$ mm.

(Fourth Modification)

Figure 23:
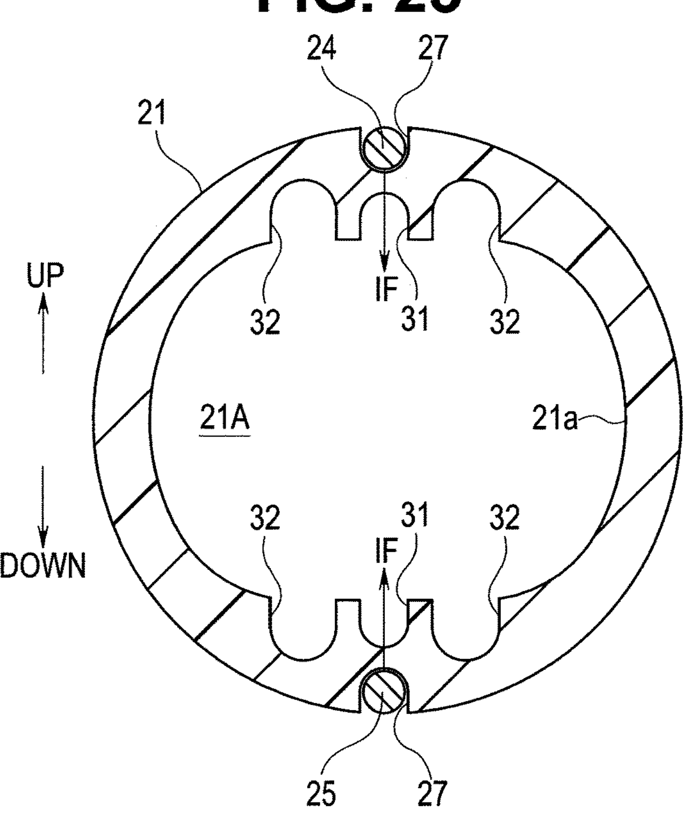
FIG. 23 is a cross-sectional view showing a configuration of a first bending piece of a bending tube of a fourth modification.
Figure 24:
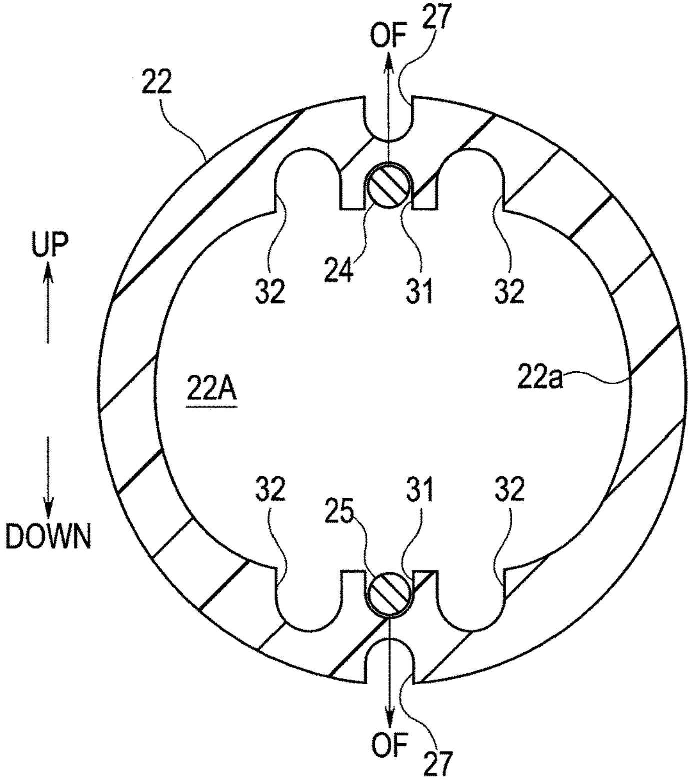
FIG. 24 is a cross-sectional view showing a configuration of a second bending piece of the bending tube of the fourth modification.

As shown in FIG. 23 and FIG. 24, a bending tube 20 of the present modification has a configuration where, in the same manner as in the third modification, each of the first bending piece 21 and the second bending piece 22 has the grooves 27, and the grooves 31 are further provided on upper and lower inner walls in the up-and-down direction of each of the inner surfaces 21*a*, 22*a*, the grooves 31 serving as wire guide portions that store the bending operation wires 24, 25 along the longitudinal axis X.

In addition to the above, each of the first bending piece 21 and the second bending piece 22 further has a plurality of, in the present modification, four recessed portions 32, being recessed, on the upper and lower inner walls in the up-and-down direction of each of the inner surfaces 21*a*, 22*a* along the longitudinal axis X, internal components not shown in the drawing, such as a light guide, an image pickup cable, and a conduit, being stored in the recessed portions 32.

The bending tube 20 has the plurality of recessed portions 32 on the inner side of each of the first bending piece 21 and the second bending piece 22 as described above, thus further increasing the inner space.

In the bending tube 20, the internal components, such as a light guide, an image pickup cable, and a conduit, are stored in the respective recessed portions 32 and hence, it is possible to restrict positions and movements of these internal components over the entire length. Therefore, it is possible to prevent the internal components, such as the light guide, the image pickup cable, and the conduit, from being broken due to interference with another internal component provided in the bending tube 20. Further, these internal components act as a framework and hence, it is possible to further enhance torque followability of the bending portion 7 in which the bending tube 20 is incorporated.

Figure 25:
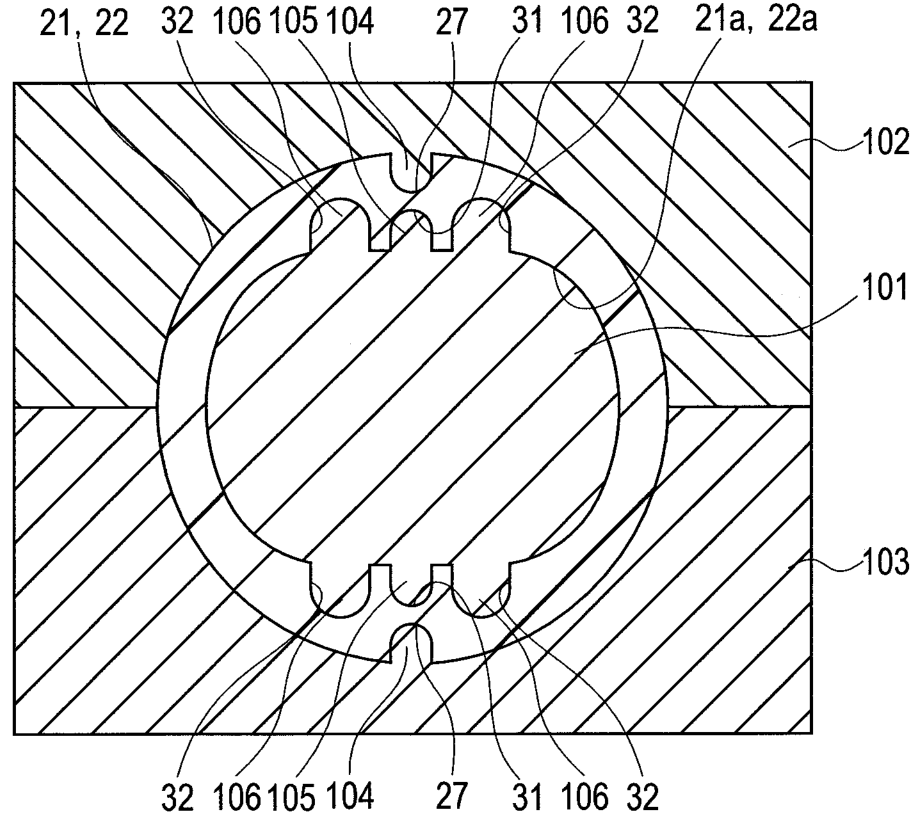
FIG. 25 is a cross-sectional view showing a portion of a mold used for forming the first bending piece and the second bending piece in the fourth modification by injection molding.

As shown in FIG. 25, each of a portion of the inner mold 101 corresponding to the first bending piece 21 and a portion of the inner mold 101 corresponding to the second bending piece 22 has a shape that includes two protruding portions 105 and protruding portions 106 on upper and lower sides of the inner mold 101, the protruding portions 105 being provided for molding the grooves 31, the protruding portions 106 being provided for molding four recessed portions 32.

The bending portion 7 is provided in the insertion portion 2 of the endoscope 1, being the above-described insertion device, and the bending tube 20 provided inside of the bending portion 7 is formed of a resin as an injection molded product. Therefore, the bending tube 20 can be manufactured at a low cost by suppressing an increase in cost caused by the bending tube 20 being formed by machining in a conventional technique.

Unlike the conventional technique, it is unnecessary to join parts made of a different material by ultrasonic welding, the parts having holes for guiding the bending operation wires 24, 25. Accordingly, the bending tube 20 has a configuration that can prevent an increase in a material cost and a processing cost.

Further, unlike the conventional technique, the bending tube 20 has a simple structure where the respective first bending pieces 21 and the respective second bending pieces 22 are connected to each other only via the coupling portions 23 without using joining members, such as rivets.

To reduce a twisting load when each first bending piece 21 and each second bending piece 22 are twisted, the bending operation wires 24, 25 are caused to lie along the outer side of each first bending piece 21 and the inner side of each second bending piece 22. Accordingly, it is possible to increase resistance against twisting.

As described above, the endoscope 1 and the bending portion 7 can achieve the bending tube 20 that is resistant against twisting and suppress a component cost and an assembly cost.

The present disclosure is not limited to the above-mentioned Embodiment, and may be suitably changed without departing from the gist and concept of the disclosure that can be read from the claims, the entire specification, and the drawings.

(Example 1) An insertion device comprising:

an insertion portion configured to be inserted into a subject and having a longitudinal axis in a state of forming a straight line;

a bending portion provided on a distal end side of the insertion portion;

a bending tube provided in the bending portion; and a pulling member configured to cause the bending portion to bend by being pulled or loosened by an operation from an outside, wherein the bending tube includes at least one first joint ring having a first contact portion where the pulling member comes into contact with an outer peripheral portion of the first joint ring, and at least one second joint ring joined to the first joint ring in an adjacent manner, and having a second contact portion where the pulling member comes into contact with an inner peripheral portion of the second joint ring.

(Example 2) The insertion device according to Example 1, wherein the bending portion includes a coupling portion configured to integrally couple a plurality of joint rings including the first joint ring and the second joint ring in a direction of the longitudinal axis.

(Example 3) The insertion device according to Example 2, wherein the first contact portion forms a first guide portion configured to guide the pulling member in the direction of the longitudinal axis on the outer peripheral portion of the first joint ring, and the second contact portion forms a second guide portion configured to guide the pulling member in the direction of the longitudinal axis on the inner peripheral portion of the second joint ring.

(Example 4) The insertion device according to Example 3, wherein the first guide portion and the second guide portion are each a groove formed to extend in the direction of the longitudinal axis on the first joint ring or the second joint ring.

(Example 5) The insertion device according to Example 4, wherein the groove is provided only on the outer peripheral portion of the first joint ring.

(Example 6) The insertion device according to Example 3, wherein the first guide portion and the second guide portion are each provided over an entire length in the direction of the longitudinal axis on the first joint ring or the second joint ring.

(Example 7) The insertion device according to Example 3, wherein at least one of the first guide portion or the second guide portion is provided on all of the first joint ring or the second joint ring.

(Example 8) The insertion device according to Example 3, wherein the second guide portion is provided only on a portion of the second joint ring.

(Example 9) The insertion device according to Example 1, wherein an inner space formed by an inner surface of the first joint ring and an inner space formed by an inner surface of the second joint ring have a same shape in cross section orthogonal to a direction of the longitudinal axis.

(Example 10) The insertion device according to Example 1, wherein the first joint ring and the second joint ring have a substantially same shape in cross section orthogonal to a direction of the longitudinal axis.

(Example 11) The insertion device according to Example 1, wherein each of an inner surface of the first joint ring and an inner surface of the second joint ring has a recessed portion in which an internal component other than the pulling member is accommodated.

(Example 12) The insertion device according to Example 1, wherein the first joint ring in plurality and the second joint ring in plurality are alternately provided in a direction of the longitudinal axis.

(Example 13) The insertion device according to Example 1, wherein the insertion device is a single-use endoscope being used once.

(Example 14) The insertion device according to Example 1, wherein the bending portion including the first joint ring and the second joint ring is molded by using a resin.

(Example 15) The insertion device according to Example 1, wherein the first contact portion extends in a direction of the longitudinal axis on an outer peripheral surface of the first joint ring, and the second contact portion extends in the direction of the longitudinal axis on an inner peripheral surface of the second joint ring.

(Example 16) A bending portion of an insertion device that is provided in an insertion portion, and that is bent when a pulling member is pulled or loosened by an operation from an outside, the insertion portion being configured to be inserted into a subject and having a longitudinal axis in a state of forming a straight line, wherein a bending tube is provided in the bending portion, the bending tube including a first joint ring having a first contact portion where the pulling member comes into contact with an outer peripheral portion of the first joint ring, and a second joint ring joined to the first joint ring in an adjacent manner, and having a second contact portion where the pulling member comes into contact with an inner peripheral portion of the second joint ring.

(Example 17) A pulling member for a bending portion of an insertion device, the pulling member causing the bending portion to bend by being pulled or loosened by an operation from an outside, the bending portion being provided in an insertion portion configured to be inserted into a subject and having a longitudinal axis in a state of forming a straight line, wherein the pulling member is disposed on a bending tube obtained by causing a plurality of first joint rings and a plurality of second joint rings to be alternately joined in a direction of the longitudinal axis, and is alternately inserted through the plurality of first joint rings and the plurality of second joint rings such that a state where the pulling member comes into contact with a first contact portion and a state where the pulling member comes into contact with a second contact portion are achieved, the first contact portion being provided on an outer peripheral portion of each of the plurality of first joint rings, the second contact portion being provided on an inner peripheral portion of each of the plurality of second joint rings.

What is claimed is:

1. A bending portion for an insertion device, comprising:

a bending tube; and a wire configured to bend the bending portion, wherein the bending tube includes:

a first joint ring, and a second joint ring joined to the first joint ring in an adjacent manner, wherein the first joint ring has a first groove entirely provided on an outer peripheral surface of the first joint ring, wherein the second joint ring has an inner peripheral surface, wherein the wire is accommodated within the first groove of the first joint ring and the wire contacts the inner peripheral surface of the second joint ring, wherein the first joint ring is configured to rotate with respect to the second joint ring, and wherein, when the bending tube is in a straight state, a bottom surface of the first groove contacted by the wire is radially outward of the inner peripheral surface of the second joint ring contacted by the wire.

2. The bending portion according to claim 1, wherein, in a direction of a longitudinal axis of the bending tube, the first joint ring is joined to the second joint ring by a coupling portion that is integrally formed with the first joint ring and the second joint ring.

3. The bending portion according to claim 1, wherein the second joint ring includes a first groove provided on the inner peripheral surface of the second joint ring and extending in the direction of the longitudinal axis, and wherein the wire is accommodated within the first groove of the second joint ring.

4. The bending portion according to claim 3, wherein the first joint ring is one of a plurality of first joint rings and the first groove of the first joint ring is provided on one or more of the plurality of first joint rings, and wherein the second joint ring is one of a plurality of second joint rings and the first groove of the second joint ring is provided on one or more of the plurality of second joint rings.

5. The bending portion according to claim 1, wherein the first joint ring has a first inner space, wherein the second joint ring has a second inner space, and wherein, in cross section orthogonal to a direction of a longitudinal axis of the bending tube, a shape of the first inner space of the first joint ring and a shape of the second inner space of the second joint ring have the same shape.

6. The bending portion according to claim 1, wherein an inner peripheral surface of the first joint ring and an inner peripheral surface of the second joint ring have a same shape in a cross section orthogonal to a direction of a longitudinal axis of the bending tube.

7. The bending portion according to claim 1, wherein each of an inner peripheral surface of the first joint ring and the inner peripheral surface of the second joint ring includes a recessed portion configured to accommodate an internal component selected from the group consisting of a light guide, an image pickup cable, and a conduit.

8. The bending portion according to claim 1, wherein the first joint ring is one of a plurality of first joint rings and the second joint ring is one of a plurality of second joint rings, and wherein a respective one of the plurality of first joint rings and a respective one of the plurality of second joint rings are alternately arranged in a direction of a longitudinal axis of the bending tube.

9. An insertion device, comprising:

an insertion portion configured to be inserted into a subject; and bending portion according to claim 1.

10. The bending portion according to claim 1, wherein the bending tube including the first joint ring and the second joint ring is formed of a resin.

11. The bending portion according to claim 1, wherein the first joint ring is one of a plurality of first joint rings and the second joint ring is one of a plurality of second joint rings, wherein a respective one of the plurality of first joint rings and a respective one of the plurality of second joint rings are alternately arranged in a direction of a longitudinal axis of the bending tube and are joined together by a respective one of a plurality of coupling portions to form a coupled first joint ring and second joint ring, and wherein a circumferential position of each coupling portion of the plurality of coupling portions is the same.

12. The bending portion according to claim 11, wherein the bending tube further includes a plurality of gaps, wherein one of the plurality of gaps is provided between each coupled first joint ring and second joint ring, and wherein a circumferential position of each of the plurality of gaps is the same.

13. The bending portion according to claim 12, wherein the circumferential position of each of the plurality of coupling portions is a first circumferential position, wherein the circumferential position of each of the plurality of gaps is a second circumferential position, and wherein the first circumferential position is different from the second circumferential position.

14. The insertion device according to claim 9, wherein the insertion device is a single-use endoscope.

15. The insertion device according to claim 14, wherein the first joint ring is one of a plurality of first joint rings and the second joint ring is one of a plurality of second joint rings, wherein a respective one of the plurality of first joint rings and a respective one of the plurality of second joint rings are alternately arranged in a direction of a longitudinal axis of the bending tube and joined together by a respective one of a plurality of coupling portions to form a coupled first joint ring and second joint ring, wherein a first circumferential position of each coupling portion of the plurality of coupling portions is the same, wherein the bending tube further includes a plurality of gaps, wherein one of the plurality of gaps is provided between each coupled first joint ring and second joint ring, wherein a second circumferential position of each gap of the plurality of gaps is the same, and wherein the first circumferential position is different from the second circumferential position.

16. The bending portion according to claim 2, wherein the wire is configured to inwardly apply a traction force to the first groove of the first joint ring in a radial direction of the bending tube.

17. The bending portion according to claim 16, wherein the second joint ring includes a first groove provided on the inner peripheral surface of the second joint ring and extending in the direction of the longitudinal axis, and wherein the wire is configured to outwardly apply the traction force to the first groove of the second joint ring in the radial direction of the bending tube.

18. The bending portion according to claim 1, wherein the first joint ring includes a second groove entirely provided on an inner peripheral surface of the first joint ring and extending in the direction of the longitudinal axis.

19. The bending portion according to claim 18, wherein the second joint ring includes a first groove entirely provided on an outer peripheral surface of the second joint ring and extending in the direction of the longitudinal axis.

20. The bending portion according to claim 1, wherein the bending tube includes a third joint ring joined to the first joint ring in an adjacent manner, wherein the third joint ring has an inner peripheral surface, wherein the wire contacts the inner peripheral surface of the third joint ring, and wherein the first joint ring is configured to rotate with respect to the third joint ring.

21. The bending portion according to claim 20, wherein the third joint ring and the second joint ring have the same shape.

22. The bending portion according to claim 1, wherein the wire is arranged to be alternately positioned at the bottom surface of the first groove of the first joint ring and at the inner peripheral surface of the second joint ring to form a radially meandering path in a longitudinal direction of the bending tube, and wherein, when a tension is applied to the wire, a radially inward force is applied to the first joint ring and a radially outward force is applied to the second joint ring.

* * * * *